United States Patent [19]

Hargreaves

[11] Patent Number: 4,868,130

[45] Date of Patent: Sep. 19, 1989

[54] METHODS FOR CONDUCTING SPECIFIC BINDING ASSAYS

[75] Inventor: William R. Hargreaves, Bellevue, Wash.

[73] Assignee: BioTope, Inc., Redmond, Wash.

[21] Appl. No.: 17,318

[22] Filed: Feb. 20, 1987

Related U.S. Application Data

[63] Continuation-in-part of Ser. No. 768,108, Aug. 21, 1985, abandoned.

[51] Int. Cl.[4] .......................................... G01N 33/546
[52] U.S. Cl. .................................... 436/526; 436/518; 436/536; 436/538; 436/806; 436/824; 435/7
[58] Field of Search ............... 436/518, 536, 538, 806, 436/824; 435/7

[56] References Cited

U.S. PATENT DOCUMENTS 4,106,907 8/1978 Charlton et al. .
4,125,375 11/1978 Hunter .
4,777,145 10/1988 Luotola .............................. 436/526

FOREIGN PATENT DOCUMENTS 1411382 10/1975 United Kingdom .
2103790 2/1983 United Kingdom ................ 436/538

OTHER PUBLICATIONS

Stephens, *Clinical Immun. and Immunopath.*, 18: 254–260 (1981).

(Abstract), *Am. J. Clin. Pathol.*, 79: 364–366 (1983).

Wiley, *Thromb. Res.*, 31: 261–268 (1983) (Abstract).

V. Bennett and D. Branton, "Selective Association of Spectrin with the Cytoplasmic Surface of Human Erythrocyte Plasma Membranes", *J. Biol. Chem.*, 252: 2753–2763, 1977.

Peter S. Linsley et al., "Detection of Larger Polypeptides Structurally and Functionally Related to Type I Transforming Growth Factor", *Proc. Natl. Acad. Sci. USA*, 82: 356–360, 1985.

J. F. Chantot and A. J. Saul, "A New Method for Measuring Binding of Labeled Ligands to Membrane Receptors", *Analytical Biochemistry*, 84: 256–262, 1978.

R. S. Yalow, "Radioimmunoassay: A Probe for the Fine Structure of Biologic Systems", *Science*, 200: 1236–1245, 1978.

*Primary Examiner*—Esther M. Kepplinger
*Assistant Examiner*—Stephen C. Wieder
*Attorney, Agent, or Firm*—Seed and Berry

[57] ABSTRACT

Methods and devices for separating bound label from unbound label within an assay mixture and for predispensing assay reactants in self-contained assay vessels, as well as a method for detecting the presence and/or amount of an analyte within a fluid sample, and a reusable detection vessel for use therein and with specific binding assays in general are disclosed. Significant to the separation of bound label from unbound label is the use of a cushion comprising generally one primary layer and in some cases one or more secondary layers.

16 Claims, 2 Drawing Sheets

METHODS FOR CONDUCTING SPECIFIC BINDING ASSAYS

CROSS-REFERENCE TO RELATED APPLICATION

This application is a continuation-in-part of applicant's copending application Ser. No. 768,108, filed Aug. 21, 1985 abandoned.

TECHNICAL FIELD

This invention relates generally to specific binding assays in self-contained assay vessels, and more particularly, to methods for storing and mixing reactants, and for separating labeled components bound to a solid phase from unbound labeled components in binding assays, followed by measurement of the bound labeled components. This invention also relates to methods for detecting the presence and/or amount of an analyte within a fluid sample using either a homogeneous or heterogeneous binding assay performed in a self-contained assay vessel, where the assay vessel contains a reaction mixture and a cushion which are predispensed in one or more layers.

BACKGROUND ART

Specific binding assays have found widespread application in the fields of biomedical research and clinical diagnostics where they are used to determine the presence or amount of a variety of substances (analytes) commonly encountered in biological fluids. Such substances may include proteins, drugs, hormones, vitamins, microorganisms, etc. In addition, specific binding assays may find utility in other fields, such as food processing and environmental quality control, for the detection of microorganisms and their toxins, or for detecting organic wastes.

Specific binding assays are commonly divided into homogeneous and heterogeneous assays. In a homogeneous assay, the signal emitted by the bound labeled component is different from the signal emitted by the unbound labeled component. Hence, the two can be distinguished without the need for a physical separation step. The classical homogeneous specific binding assay is the enzyme-multiplied immunoassay technique (EMIT), described in U.S. Pat. No. 3,817,837, issued to Rubenstein.

Homogeneous specific binding assays are rapid and easy to perform, either manually or with automated instruments. However, these tests typically require sequential additions and mixing, with intervening incubations, of sample plus antibody, then enzyme-analyte conjugate, followed by enzyme substrate color developer solution. Automation has been achieved with various types of analyzers including discrete (e.g. DuPont aca ™), centrifugal (e.g. Roche Cobas Bio ™), and linear flow (e.g. Technicon SMAC ™). However, homogeneous assays have several disadvantages: they are typically limited to detection of low molecular weight compounds, are prone to interferences, and are generally limited in sensitivity to detection of approximately nanomolar analyte.

In heterogeneous assays, both large and small analytes can be detected, but the signal emitted by the bound and unbound labeled components is identical, hence the two must be physically separated in order to distinguish between them. The classical heterogeneous specific binding assay is the competitive radio immunoassay (RIA), described by Yalow (*Science* 200:1245, 1978). Other heterogeneous binding assays are the radioreceptor assay, described by Cuatrecasas (*Ann. Rev. Biochem*, 43: 109–214, 1974), and the sandwich radioimmunoassay, described by Wide (pp. 199–206 of *Radioimmunoassay Methods,* Edited by Kirkham and Hunter, E. & S. Livingstone, Edinburgh, 1970). Because interferences are usually eliminated, and because excess binding reagents can sometimes be used, heterogeneous binding assays can be significantly more sensitive and reliable than homogeneous assays.

In a typical "double antibody" competitive RIA, a known amount of radiolabeled ligand and ligand present in the sample compete for a limited amount of antibody. Sufficient time is allowed for specific binding to occur, after which the antibody and bound ligand are precipitated by addition of anti-immunoglobulin, washed to remove unbound label by repeated centrifugation, and the amount of labeled ligand present in the bound phase is determined.

A sandwich assay can be used to achieve greater sensitivity for analytes such as antigen in an immunoassay. In such an assay, excess ligands are used to force binding at concentrations below the dissociation constant of the binding pair. In the typical sandwich immunoassay, two antibody types are required, each of which can bind simultaneously to the antigen. One antibody is bound to a solid phase, while the other is labelled. As with competitive RIAs, one or more discrete washing steps to separate bound and unbound label are required, and sequential addition of reagents is typical.

Because the solid phase must be isolated and washed, and because sequential reagent additions are frequently required, heterogeneous assays tend to be time consuming and labor-intensive. However, they work equally as well for low and high molecular weight compounds, are less prone to interferences than homogeneous assays, and can be sensitive to sub-picomolar antigen concentrations. Automation of heterogeneous immunoassays has been accomplished (ARIA II ™ by Becton Dickinson, CentRIA ™ by Union Carbide), but this has required either sophisticated and expensive instrumentation to carefully control liquid flow and to monitor bound and unbound fractions, or it has resulted in the detection only of the unbound label flowing through a rapidly hydrated antibody solid phase.

Several attempts have been made to eliminate the inconvenience of washing steps in heterogeneous binding assays. For example, Glover et al., GB No. 1,411,382, describe a method for measuring the amount of unbound radiolabel, after partial separation from bound label, by shielding the bound (lower) phase. However, it is well known in the art that the sensitivity and precision of specific binding assays is severely limited if changes in the unbound rather than the bound labeled component are measured. Furthermore, methods which lack a washing step have the disadvantage of detecting both tightly binding (specific) and weakly binding (nonspecific) label, resulting in very high nonspecific signal. Charlton et al., U.S. Pat. No. 4,106,907, issued Aug. 15, 1978, disclose another container for radioactive counting which consists of a tapered reaction tube having a radiation shield extending up from the bottom of the tube to a uniform height, such that only radiation from the supernatant (the unbound labeled fraction) can be detected. This method is subject to the same limitations as Glover et al., supra.

Chantot et al., *Analyt. Biochem.* 84:256, 1978, describe a radioreceptor assay method for measuring the binding of radiolabeled ligands to membrane receptors. The technique involves counting the total amount of radiolabel present, centrifuging the sample, and recounting with an externally mounted copper screen which serves to absorb radiation from a defined volume of the supernatant. The screen itself consists of a copper sleeve mounted on the outside of a custom-made test tube having a small knob precisely positioned above the base to support the screen. This method suffers from the disadvantage of requiring double detection, and suffers as well from high nonspecific binding as described above for the Glover and Charlton methods. Furthermore, the tube is vulnerable to jamming and breakage in standard gamma counters. As with the above-described 'screening' methods, the large diameter of the screen allows significant scattered radiation from within the screened volume to impinge on the detector, resulting in inaccurate measurements of the unscreened label. Also, because bound label is directly adjacent to and in contact with unbound label, normal and unavoidable variability in the position of the screen or in the volumes of the unbound and bound phases can cause significant variability in signal.

Bennett et al., (*J. Biol. Chem.* 252: 2753, 1977) describe a radioreceptor assay in which, after mixing and incubating reagents, the assay mixture is transferred to a centrifuge tube to wash the solid phase containing bound label. They employed prolonged (30 minutes) high speed centrifugation to force the solid phase into a solution of 20% sucrose, followed immediately by freezing the assay tube in liquid nitrogen and excising the tip of the tube containing the solid phase and bound label. This method provides more effective separation of bound and unbound label than those described above, but has several significant disadvantages. The assay mixture cannot be incubated in situ on top of the sucrose solution, thus requiring separate incubation and separation vessels, because reactants would diffuse into the solution. Care must be used in loading the assay mixtures onto these sucrose solutions because mixing will cause dilution of the assay mixture, thus changing the equilibrium for assay reactants. The separation is relatively lengthy, and assay tubes must be frozen immediately after centrifugation because the bound label can dissociate from the solid phase and diffuse away from the tip of the separation tube. Finally, excising the tip of separation tubes is inconvenient, time-consuming, difficult to perform reproducibly, exposes the user to the risk of liquid nitrogen burns and radioactive contamination from fragments of frozen tubes and their contents, and would be very difficult to automate.

In U.S. Pat. No. 4,125,375 (issued Nov. 14, 1978), Hunter describes a method and automated instrumentation for performing heterogeneous immunoassays by carefully injecting a sucrose solution underneath a previously equilibrated immunoassay mixture containing particles of higher density than the sucrose solution. The particles are allowed to settle through the injected subphase, thereby separating the particles from the unbound label. This method potentially eliminates some of the disadvantages inherent in the Bennett et al. method but suffers from several significant shortcomings. These shortcomings include that: (1) it requires separate preequilibration of the assay mixture prior to separation of bound and free label, plus removal of liquid waste, and thus cannot be self-contained, (2) the method is not readily adaptable to the most rapid (centrifugal) separations, (3) it suffers from potential dilution and diffusion artifacts as in the Bennett et al. method, (4) it is not suitable for convenient and reproducible manual assays, and (5) any automated instrument would require Linsley et al., *Proc. Natl. Acad. Sci.* (USA) 82: 356, 1985, describe a radioimmunoassay for type I transforming growth factor using *S. aureus* in which the bound label is separated from the unbound label by rapid sedimentation into a solution of 10% sucrose, followed by freezing in liquid nitrogen and excision of the tip of the centrifuge tube to determine the sedimented bound label. This method is essentially an immunoassay embodiment of the radioreceptor assay described by Bennett et al., with the inherent disadvantages of the former method.

Although each of the methods described above have brought minor improvements to the state of the art, there remains a need in the art for a method of specific binding assay which combines the ease and rapidity of homogeneous techniques with the enhanced sensitivity typical of heterogeneous techniques, for both isotopic and nonisotopic applications, without the undesirable variability, delay, labor, and dissociation which occur during the wash steps. Further, the method should allow rapid separations, should be convenient for manual use with standard detection instruments, and should be readily adaptable to semiautomated or fully automated instrumentation. Ideally the method should be self-contained, have minimal plumbing and moving parts, and be compatible with fully predispensed reagents. The present invention fulfills this need, and further provides other related advantages.

DISCLOSURE OF THE INVENTION

Briefly stated, the present invention discloses methods and associated devices for separating bound label from unbound label within a binding assay mixture, and for predispensing a cushion in one or more liquid or solid layers, as well as a reaction mixture, which, with the addition of sample, forms a self-contained system for both heterogeneous and homogeneous binding assays. In addition, methods for detecting the presence and/or amount of an analyte within a fluid sample, assay vessels, and a reusable detection vessel for use therein and within specific binding assays in general are disclosed. For purposes of the present invention, the term 'cushion' is defined to include all primary and secondary layers within any one embodiment.

In one aspect of the present invention, a method is disclosed for separating bound label from unbound label within an assay mixture formed within an assay vessel. For purposes of the present invention, the phrase "assay mixture" includes a reaction mixture, having at least label and binding components, and sample. The assay mixture can be in the form of one or more layers in an assay vessel, a layer being in the form of a droplet, or varying from a thin film to several centimeters thick depending on the volume of the assay mixture and the dimensions of the assay vessel. The assay mixture generally comprises a reagent mixture plus a sample containing analyte. The reagent mixture further comprises one or more binding components and may further comprise one or more labels. Binding components normally comprise two parts: a solid phase and a specific binding agent attached thereto, which confers specific binding activity. Additional specific binding agents may be present which are not initially attached to the solid phase, as long as substantially all of the additional binding agent becomes attached to the solid phase prior to separation of bound label from unbound label. In addition, other binding agents may be added subsequent to separation of bound label from unbound label.

Once the reagent mixture and sample are combined to form the assay mixture, an incubation period is usually required. The incubation period can range from one second to several days, depending in part upon factors such as the sensitivity required, and the binding affinity and concentration of binding components. Following incubation of the assay mixture, at least some label and/or analyte is bound to at least some of the binding components. The incubated assay mixture typically includes some unbound label and/or unbound analyte and in addition also includes other components such as water, buffer, preservative, and proteins, these components typically comprising a largely aqueous solution.

As an alternative to forming the complete assay mixture within an assay vessel, an assay mixture may be prepared outside of the assay vessel. This alternative is appropriate for non-isotopic binding assays, thereby avoiding the potential hazards associated with handling of radioisotopes outside of the assay vessel. This alternative is especially advantageous, for instance, when automated liquid-handling apparatus is available to the user for dispensing reagents.

Briefly, these methods comprise (a) contacting a primary layer with an assay mixture, both the binding components and the unbound label being immiscible with the primary layer and the binding components being of a different density than the primary layer; and (b) subjecting the assay mixture in contact with the primary layer to conditions sufficient to cause the binding components and the unbound label to separate. Typically the binding components have a density greater than that of the primary layer and the aqueous solution component of the assay mixture has a density less than or equal to that of the primary layer. In some embodiments, barrier layer (preferably selectively liquifiable) is positioned between the assay mixture and the primary layer. The barrier layer, when liquified, is miscible with the assay mixture, while in the solid or gel form, it serves to separate the reaction mixture from the primary layer. A barrier layer is especially useful when predispensing of reagents is desired with an embodiment utilizing a liquid primary layer.

In particular embodiments, either or both the binding components and the unbound label may be of the same density as the primary layer. In one such embodiment, the binding components are formed by immobilizing specific binding agents to the surface of a vessel containing the remainder of the assay mixture, and thus the density of the binding components is not relevant to the assay. In another such embodiment, the binding components are magnetic particles and are separated from unbound label by magnetic forces. In such cases, the binding components need not differ significantly in density from the primary layer, though typically the aqueous solution component of the assay mixture will have a density less than that of the primary layer.

In additional embodiments, which are typically homogeneous binding assays, the density of the entire assay mixture may be greater than the density of the primary layer. One such embodiment utilizes a barrier layer or a selectively liquifiable primary layer which is in a solid form during the addition of sample and incubation, and is then liquified to allow mixing of the assay mixture with a secondary layer containing additional reagents such as enzyme substrate color developer.

In a related embodiment of the present invention which includes the predispensing of the cushion and the reaction mixture, the reaction mixture is contacted with the primary layer, as described above, substantially prior to the addition of sample and the subsequent incubation of the assay mixture. For both heterogeneous and homogeneous binding assays, this provides advantages to the user of greater convenience compared to assays where each reactant must be dispensed as needed. Furthermore, where precise and automated equipment is used to predispense the assay reactants during manufacture of the assay system, greater precision is to be expected compared to manual dispensing of reactants by the user as they are needed.

In some embodiments, one or more reactants are contained separately from the reaction mixture in the assay vessel. For example, in a competitive immunoassay, label and binding components, specifically antibody-capture binding components, may be predispensed to form a reaction mixture. Following addition of sample to the reaction mixture, the reaction is initiated by addition of analyte-specific antibody. This analyte-specific antibody, which is typically a solution, can be contained in a reagent reservoir prior to initiation of the reaction. For example, as will be discussed more fully below, a secondary layer in the cushion can serve as a reagent reservoir containing additional reaction components. Alternatively, a hollow cap having a removable seal may be provided to serve as a reagent reservoir. One kind of seal could be fashioned by providing a small orifice in the hollow cap, where the orifice is plugged with a selectively liquifiable material (preferably water-immiscible). A moderate force such a air pressure or low-speed centrifugation could be employed to force the liquid from the cap reservoir into the reaction mixture.

In a related aspect of the present invention, a method is disclosed for detecting the presence and/or amount of an analyte within a fluid sample using either a homogeneous or heterogeneous binding assay performed in a self-contained assay vessel. The assay vessel typically contains assay reactants which are predispensed in one or more layers. I n some embodiments for detecting the presence or amount of analyte within a fluid sample, the label may comprise the analyte itself, where the analyte is capable of emitting a detectable signal. Such analytes include hemoglobin as well as enzymes (prostatic acid phosphatase, creatine kinase).

For example, an assay for detecting the percentage of glycosylated hemoglobin present in blood typically involves separating most or all of this analyte from a blood sample using a binding component in the form of an ion exchange or affinity column, then measuring the absorbance of the bound analyte (glycosylated hemoglobin) as well as the absorbance of the unbound label (which includes nonglycosylated hemoglobin) using a suitable colorimeter. In this embodiment, the same particles used in commercially available columns (Pierce, Rockford, Ill.) can be used as binding components in the present invention. After a suitable incubation, the assay mixture is subjected to conditions sufficient to cause the binding components and the unbound label to separate and the bound label (analyte) is detected. Preferably both bound and unbound label are measured to allow the calculation of the percentage of analyte which is bound. The bound label may be eluted from the particles (such as with a sugar solution for glycosylated hemoglobin), prior to the absorbance measurement.

In an additional related aspect of the present invention, several devices for separating bound label from unbound label within an assay mixture as described above are disclosed. In one embodiment, the device comprises an assay vessel having an open proximal end, preferably resealable, and a closed distal end, the vessel defining an elongated chamber therewithin. In another embodiment, the device comprises a multiwell plate. In a further embodiment, the device comprises elongated assay vessels or strips of connected elongated assay vessels. The assay vessels are typically positioned such that they have substantially the same spacing as the wells in a multiwell plate. These devices have a primary layer which most often extends generally transversely within the chamber or across the well to form a selective barrier therein, the primary layer being immiscible with both the binding components and the unbound labile, and typically of different density than the binding components. For narrow, elongated vessels, the orientation can be vertical, horizontal, or intermediate between the two extremes without mixing any liquid layers. The assay vessel may also contain a barrier layer positioned between the proximal end and the primary layer.

In another aspect of the present invention, an alternative method is disclosed for detecting the presence or amount of an analyte within a fluid sample. Briefly, the method comprises (a) incubating the fluid sample with a reagent mixture to form an assay mixture, the assay mixture being formed within an assay vessel, with the assay mixture containing one or more binding components, label, analyte, and other components, and with at least some of the label and some of the analyte binding, directly or indirectly, to the binding components; (b) contacting a primary layer with the assay mixture, the binding components having label and/or analyte bound thereto, and the unbound label being immiscible with the primary layer; (c) subjecting the assay mixture in contact with the primary layer to conditions sufficient to cause the binding components and the unbound label to separate; and (d) detecting the label bound to the binding components and therefrom determining the presence or amount of the analyte.

A particularly preferred embodiment of the method disclosed above comprises contacting the primary layer with the fluid sample and reagent mixture prior to incubation of the resultant assay mixture. Within this embodiment, the formation and incubation of the assay mixture occurs in the assay vessel in which the separation is carried out.

An additional preferred embodiment of the method disclosed above comprises including, in one or more secondary layers, supplementary assay components which are preferably added to the binding components after bound label is separated from unbound label. Supplementary assay components may include label such as an enzyme-conjugated antibody, specific binding agent such as unconjugated antibody, enzyme substrate color developer, and enzymes such as proteases. Other substances contained in secondary layers such as those listed in Table 2 may be considered, in some cases, to be supplementary assay components if they perform an additional function beyond adjusting the density of the secondary layer solution.

An additional aspect of the present invention discloses a reusable detection vessel for use in specific binding assays which use radioactive labels. The detection vessel generally comprises an elongated container having an open end and a closed end, and a radiation shield adapted to fit within the elongated container and positioned therein to provide a shielded portion, and an unshielded portion toward the closed end. In most instances it is preferable to use a shield which has a substantially cylindrical bore, which better provides effective and uniform shielding. Although not essential, it may be convenient to provide the shield with a cylindrical exterior. In one embodiment, this design allows a portion of an assay vessel, which has been inserted into the detection vessel, to protrude downward from the shield a distance sufficient to allow detection of the label within the exposed portion of the assay vessel. In another embodiment, the detection vessel is provided with a substantially cylindrical member positioned between the shield and the distal end of the container, the cylindrical member being adapted to support and maintain the position of the shield within the container. In still another embodiment, the cylindrical member is closed at the distal end to support an additional thin radiation shield in the form of a disk. The disk allows more effective shielding when using certain detection instruments such as certain well-type gamma counters.

Other aspects of the present invention will become evident upon reference to the following detailed description and attached drawings.

BEST MODE FOR CARRYING OUT THE INVENTION

Figure 1A:
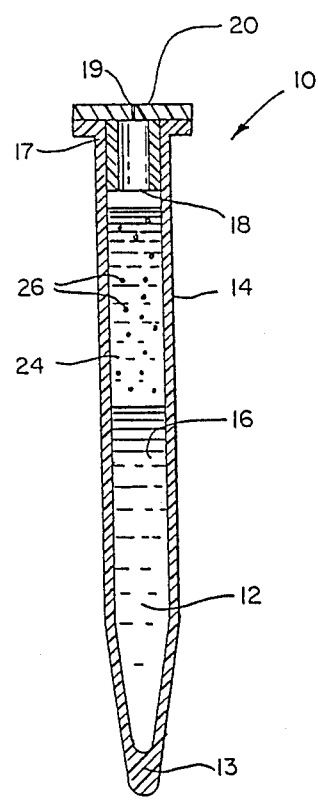
FIG. 1A is a side elevation view of an assay vessel and related closures of the present invention.

The following terms are defined herein for clarity:

Reaction Component a substance or reagent which participates in and is a component of the binding assay; typically one of several solvents, solutes, or solids which are mixed to form a reaction mixture, and/or with sample to form an assay mixture. A reaction component also may be stored within a reagent reservoir.

Reagent Reservoir an enclosure, matrix, or device in the assay vessel in which reaction components are predispensed or stored, separate from the reaction mixture or the assay mixture. A reagent reservoir may be located distal to the primary or a secondary later, relative to the proximal end of the assay vessel, or within a secondary layer. Alternatively, it may be located in or adjacent to the proximal end of the assay vessel.

Reaction Mixture the primary solution or suspension of reaction components which, upon addition of sample, becomes the assay mixture. The reaction mixture is typically in contact with or in proximity to the primary layer, and includes at least label and binding components.

Assay Mixture the combination of a reaction mixture with a sample results in the formation of an assay mixture. Other reaction components may be subsequently added.

Binding Components include specific binding agents (such as antibody) and a solid phase (nascent or preformed, particulate or a continuous surface).

Cushion includes the primary and any secondary layer(s), as well as any assay components which are not in the reaction mixture or assay mixture, except those that are contained in one or more discrete reagent reservoirs.

Primary Layer a substance which is not miscible with water, and extends generally transversely within an assay vessel (typically in contact with the assay mixture), and serves to separate bound from unbound label by allowing the penetration of binding components without allowing the penetration of unbound label. Generally, the primary layer is a liquid in the temperature range of 15°–50° C. Preferred are primary layers which are selectively liquifiable.

Secondary Layer any layer or material distal from the primary layer relative to the assay reaction mixture, assay mixture, or proximal end of the assay vessel. A secondary layer may be water miscible or immiscible, and may comprise a solid or liquid. Typically a secondary layer is in a liquid form in the range of 15°–50° C. Desirable secondary layers are selectively liquifiable.

Barrier Layer located between a reaction or assay mixture and the primary layer, the barrier layer serves to prevent contact and/or mixing between the mixture(s) and the primary layer, is selectively liquifiable, and in its liquid form is miscible with the aqueous solution of the reaction mixture.

Selectively Liquifiable

A substance is selectively liquifiable when it can be reversibly converted to a liquid from a solid or gel. Generally this is accomplished by melting, in the temperature range of 15°–50° C.

As noted above, heterogeneous specific binding assays are typically more sensitive than homogeneous assays. However, in practice this advantage is often outweighed by the labor-intensive and time consuming manipulations of the assay mixture which are typically required. Even with homogeneous assays, several separate, sequential additions of assay reagents are often required. The present invention is concerned with materials and methods for the performance of more convenient and less labor-intensive specific binding assays, including both homogeneous and heterogeneous assays. Such binding assays can be performed manually or with automated instruments designed to perform homogeneous or heterogeneous assays. In heterogeneous assays, a binding component is employed which comprises a solid phase and attached specific binding agent, and typically binds at least some of the label to produce both bound and unbound label. In homogeneous assays, a binding agent is employed which is typically dissolved in solution.

An important advantage for heterogeneous assays provided by the present invention is that either the reagent mixture or the assay mixture (which includes sample) can be stored or incubated in contact with a barrier layer or a primary layer. Such storage of the reagent mixture is advantageous because it allows the reaction components and cushion to be prepackaged. This reduces the number of manipulations by the user in preparing for and performing the assay, and can improve both convenience, speed, and precision. Because separate storage of wash buffer as well as collection and disposal of waste liquids are eliminated, the present invention reduces the space requirements and increases the safety of laboratory testing. Furthermore, field testing is facilitated because no water is required.

Another important advantage provided by the present invention which is relevant to both homogeneous and heterogeneous enzyme-labeled assays is that supplementary assay components can be predispensed in one or more layers separate from the assay mixture layer, to create a completely self-contained assay vessel for determining the presence and/or level of an analyte. In the prior art, such supplementary assay components (for example, enzyme substrate color developer for homogeneous assays, and labeled antibody in sandwich immunoassays) typically are added after an incubation step and in some cases after the separation of bound from unbound label and/or analyte. There exists significant commercial advantage in the present invention for predispensing all assay reactants so that such features as user convenience as increased compared to the prior art.

In another aspect, the invention is concerned with methods and devices for selectively measuring bound label after the separation has been performed. In some embodiments, measurement of bound label is facilitated by shielding the unbound label from the detector.

A. Barrier Layers

The barrier layer serves to prevent contact and/or mixing between the mixture(s) and the primary layer, typically is selectively liquifiable, and in its liquid form is miscible with the aqueous solution of the reaction mixture. It is located between a reaction or assay mixture and the primary layer. The preferred barrier layer is an agarose or gelatin gel which can be melted in the temperature range of 15°–50° C. Barrier layers for other applications have been described in U.S. Pat. No. 4,522,786 (issued June 11, 1985, to R. C. Ebersole), which is herein incorporated by reference.

B. Primary and Secondary Layers of the Cushion

The methods of this invention generally employ a largely aqueous assay mixture containing a binding component and label, and a primary layer. A primary layer is immiscible with water and extends generally transversely within an assay vessel (typically in contact with the assay mixture). Generally, the primary layer is a liquid in the temperature range of 15°–50° C. Preferred are primary layers which are selectively liquifiable. One or more secondary layers may also be employed.

The primary layer serves at least one of two functions depending on whether the binding assay is homogeneous or heterogeneous. In a heterogeneous assay, the primary layer serves to separate bound from unbound label by allowing the penetration of binding components without allowing the penetration of unbound label. In a homogeneous assay, the primary layer separates the reaction and assay mixtures from other reaction components which must be added to the assay mixture after an initial incubation step. Under suitable conditions, the assay mixture passes through the primary layer to contact or mix with other reaction components such as enzyme substrate color developer.

In certain cases a composite primary layer can be produced which has certain surprising advantages. For example, a primary layer of diphenyl methane (DPM) is selectively liquifiable, with a melting temperature of approximately 26° C. However, the density of liquid DPM is almost the same as water (1.001 at 26° C.) and less dense than many reaction mixtures or assay mixtures. Thus for such cases, the aqueous mixture itself may pass through the primary layer after it is liquified by warming, without causing the separation of binding components from unbound label.

However, solidified DPM can be exploited by combining it with liquid primary layer material of different (typically greater) density, to form a composite primary layer. For example, if DPM is layered on a dense aqueous secondary layer and chilled to solidify the DPM, then a liquid primary layer material such as diethylmethylmalonate (d=1.013) can be layered on top of the DPM. This forms a composite primary layer with both liquid ("high density") and solid ("low density") components. When reagents or sample is pipetted into the vessel, the solid layer at the bottom of the composite primary layer prevents mixing of the reagents and/or sample with the secondary layer(s). For this mixture, warming at room temperature (20°-22° C.) for 15-20 minutes results in liquification of the primary layer.

The barrier layer, if present, and the cushion are in a liquid form, at least during the separation of bound from unbound label by the primary layer and during any subsequent steps in which binding components penetrate additional layers. The primary layer is also largely or totally immiscible with the assay mixture. These two features allow effective contact of the binding components with the primary layer, with the concomitant exclusion of the aqueous components of the assay mixture. In many embodiments, the primary and secondary layers may also be of a density different than the assay mixture (typically the densities are greater than that of the assay mixture), so that the relative positions of the assay mixture and the cushion layers can be maintained under the forces of gravity or centrifugation.

Separated from the assay mixture layer by the primary layer, one or more additional layers may be employed which may be miscible or immiscible with aqueous solutions. These additional layers are hereinafter referred to as "secondary layers". Each secondary layer typically is of different density than the other layers employed, and in addition is largely or totally immiscible with any adjacent layers. In general, all layers should be resistant to mixing or inversion, or should return to their relative positions on brief standing. This can be achieved by selecting at least one layer material which is a solid at the temperature of storage, or by using layers which differ greatly in density and are immiscible (e.g. butyl phthalate and fluorocarbon oil) Miscible mixtures of materials such as those materials listed in Table 1 also have useful properties. For example, by blending two or more substances which melt higher than 50° C. one could obtain a eutectic mixture with a desirable density and a desirable melting temperature in the 15°-50° C. range.

Surprisingly, the inclusion of detergent in one or more layers or in the assay mixture in some cases facilitates spontaneous separation of mixed liquid layers. Suitable detergents include nonionic (such as Nonidet P-40 or Triton X-100) and ionic detergents (such as taurodeoxycholate or dodecyl sulfate) and various mixtures of detergents.

The primary layer can be composed of any of a variety of compounds provided that it is substantially immiscible with the components of the assay mixture, and typically will have a liquid density different than the solid and liquid components of the assay mixture. In instances where the primary layer has a density equal to or greater than the aqueous solution of the assay mixture, the density of the primary layer is usually approximately 1.01 or greater. For such instances involving centrifugal separations, the density of the primary layer typically does not exceed 1.20, and is most preferably greater than 1.03 and less than 1.15. Furthermore, for heterogenous binding assays the density of the primary layer typically will be less than the apparent density of the binding components. In addition, the primary layer will be in a liquid form at least for the separation step or supplementary reagent mixing step following incubation. Secondary layers also will be in a liquid form, at least for any supplementary reagent mixing steps, and-/or during such periods that the binding components are desired to penetrate or pass through the secondary layers. Liquification of solid primary layers typically involves melting, generally in the range of 15°-50° C. In applications utilizing gravity or centrifugation to achieve separations in heterogeneous binding assays, or where a supplementary reagent mixing step is desirable in homogeneous binding assays, the density of the primary and any secondary layers should be different than the density of the assay mixture. A representative listing of water-immiscible dense oils suitable for use as primary layers is shown in Table 1. These materials may also be used as components of secondary layers.

For embodiments where the primary layer is more dense than the liquid components of the assay mixture, the primary layer materials will have the properties of oils with densities greater than water (d>1.00).

TABLE 1

| | REPRESENTATIVE LIST OF WATER-IMMISCIBLE SUBSTANCES | | | | | |
|---|---|---|---|---|---|---|
| ITEM | CHEMICAL NAME | MERCK#(9TH ED) OR VENDOR | DENSITY | MP/FP | MolWt | SOLUBILITY (parts H$_2$O) |
| 1 | ETHYL ACETOACETATE | 3686 | 1.03 | −45 | 130 | 35 |
| 2 | ETHYL ACETYLSALICYLATE | 3687 | 1.15 | N.A. | 208 | INSOL |
| 3 | METHYL ADIPATE | ALDRICH | 1.06 | 8 | 174 | N.A. |
| 4 | ETHYL ADIPATE | 3689 | 1.01 | −18 | 202 | INSOL |
| 5 | METHYL BENZOATE | 5899 | 1.09 | −15 | 136 | INSOL |
| 6 | ETHYL BENZOATE | 3697 | 1.05 | −34 | 150 | ALMOST INSOL |
| 7 | ETHYL BENZOYLACETATE | 3698 | 1.12 | N.A. | 192 | INSOL |
| 8 | ETHYL BENZENESULFONATE | 3696 | 1.22 | N.A. | 186 | SLIGHTLY |

TABLE 1-continued
REPRESENTATIVE LIST OF WATER-IMMISCIBLE SUBSTANCES

| ITEM | CHEMICAL NAME | MERCK#(9TH ED) OR VENDOR | DENSITY | MP/FP | MolWt | SOLUBILITY (parts H$_2$O) |
|---|---|---|---|---|---|---|
| 9 | METHYL CARBONATE | 5912 | 1.06 | 0.5 | 90 | INSOL |
| 10 | METHYL CINNAMATE | 2288 | 1.04 | 36 | N.A. | ALMOST INSOL |
| 11 | ETHYL CINNAMATE | 2288 | 1.04 | 8 | N.A. | INSOL |
| 12 | BUTYL CINNAMATE | 2288 | 1.01 | N.A. | N.A. | 200 |
| 13 | TRIETHYL CITRATE | 3719 | 1.14 | N.A. | 276 | 14.5 |
| 14 | BUTYL CITRATE | 1551 | 1.04 | −20 | 360 | INSOL |
| 15 | DIMETHYL FUMARATE | ALDRICH | N.A. | | 103 | |
| 16 | DIETHYL FUMARATE | ALDRICH | 1.05 | 1–2 | 172. | N.A. |
| 17 | METHYL FUROATE | 5943 | 1.18 | N.A. | 126 | SLIGHTLY |
| 18 | DIETHYL GLUTACONATE | SIGMA | 1.05 | N.A. | N.A. | N.A. |
| 19 | DIMETHYL GLUTARATE | 4305 | 1.09 | N.A. | 160 | N.A. |
| 20 | DIETHYL GLUTARATE | ALDRICH | 1.02 | N.A. | 188 | N.A. |
| 21 | DIMETHYL ITACONATE | ALDRICH | 1.12 | 37–40 | 158 | N.A. |
| 22 | DIETHYL MALEATE | 3761 | 1.06 | −10 | 172 | INSOL |
| 23 | DIETHYL ACETAMIDOMALONATE | ALDRICH | N.A. | | 97 | |
| 24 | DIMETHYL MALONATE | 5961 | 1.16 | −62 | 132 | SLIGHTLY |
| 25 | DIETHYL MALONATE | 3763 | 1.06 | −50 | 160 | 50 |
| 26 | DIETHYL METHYL MALONATE | SIGMA | 1.01 | N.A. | N.A. | N.A. |
| 27 | DIETHYL BENZYL MALONATE | ALDRICH | 1.06 | N.A. | 250 | N.A. |
| 28 | ETHYL OXALACETATE | 3776 | 1.30 | N.A. | 188 | INSOL |
| 29 | DIMETHYL OXALATE | ALDRICH | 1.15 | 50–54 | 118 | 17 |
| 30 | DIETHYL OXALATE | 3109 | 1.08 | −41 | 146 | SPARINGLY |
| 31 | ETHYL PHENYLACETATE | 3780 | 1.03 | N.A. | 164 | N.A. |
| 32 | DIMETHYL PHTHALATE | 3244 | 1.19 | 0 | 194 | 232 |
| 33 | DIETHYL PHTHALATE | 3783 | 1.23 | N.A. | 222 | INSOL |
| 34 | DIPROPYL PHTHALATE | ALDRICH | 1.08 | N.A. | 250 | N.A. |
| 35 | DIBUTYL PHTHALATE | 1575 | 1.04 | −35 | 278 | 2500 |
| 36 | METHYL SALICYLATE | 5990 | 1.18 | −8.6 | 152 | 1500 |
| 37 | ETHYL SALICYLATE | 3793 | 1.13 | 1 | 166 | SLIGHTLY |
| 38 | DIMETHYLDIPHENYLPOLYSILOXANE | SIGMA | 1.05 | N.A. | N.A. | INSOL |
| 39 | SILICONE OIL | SIGMA | 1.05 | N.A. | N.A. | INSOL |
| 40 | DIMETHYL ACETYL SUCCINATE | ALDRICH | N.A. | | 33 | |
| 41 | DIETHYL ACETYL SUCCINATE | ALDRICH | N.A. | | N.A. | |
| 42 | DIMETHYL SUCCINATE | 5993 | 1.12 | 19.5 | 146 | 120 |
| 43 | DIMETHYL METHYL SUCCINATE | ALDRICH | 1.08 | N.A. | 160 | N.A. |
| 44 | DIETHYL SUCCINATE | 3799 | 1.04 | −21 | 174 | insol |
| 45 | DIMETHYL L-TARTRATE | ALDRICH | 1.24 | 48–50 | 178 | N.A. |
| 46 | DIETHYL L-TARTRATE | 3803 | 1.20 | 17 | 206 | slightly |
| 47 | DIBUTYL L-TARTRATE | ALDRICH | 1.09 | 21–22 | 262 | N.A. |
| 48 | FLUORINERT FC-40 (3M) | 3M | 1.85 | N.A. | N.A. | INSOL |
| 49 | FLUORINERT FC-70 (3M) | 3M | 1.93 | N.A. | N.A. | INSOL |
| 50 | FLUORINERT FC-77 (3M) | 3M | 1.78 | N.A. | N.A. | INSOL |
| 51 | DIPHENYLMETHANE | 3339 | 1.00 | 26 | 168 | N.A. |

However, for some homogeneous binding assays requiring a supplementary reagent mixing step, in which the entire reaction mixture penetrates the primary layer to mix with one or more supplementary assay components in a secondary layer, an oil with a density less than or equal to water can be employed if it can be maintained in a solid form during incubation, then subsequently liquified. In such embodiments, the reaction mixture may contain one or more materials which form dense aqueous solutions. A representative list of such water-miscible materials forming dense aqueous solutions is shown in Table 2.

Dense oil-like materials are typically synthetic esters (usually methyl, ethyl, propyl or butyl) of bioorganic acids, and usually contain substantial oxygen, nitrogen, or sulfur, or they are fluorocarbon oils or silicon-based oils. Most dense oil-like materials are miscible with each other and can be used alone or in various mixtures in primary or secondary layers. However, in some embodiments it is possible and desirable to create adjacent water-immiscible layers which are not miscible with each other and which differ in density (e.g. a hydrocarbon-based material or mixture plus a fluorocarbon-based material or mixture). In such embodiments a water-immiscible layer which is not in contact with the assay mixture would be called a secondary layer.

To those experienced in organic chemistry and others skilled in the art, related water-immiscible materials which have desirable properties, other than those materials listed in Table 1, will be readily apparent. Such properties include partial or complete immiscibility in water and aqueous solutions and lack of objectionable odor or toxicity. A further desirable property of a primary layer material is the ability to rapidly and spontaneously reform a homogeneous phase when mixed with a reagent mixture or assay mixture. Further, the primary layer must be in a liquid form during the separation step (in heterogeneous assays) and the supplementary reagent mixing step (in homogeneous assays).

While most of the applications described for the present invention can utilize dense oils as primary layer materials, it will be apparent to those skilled in the art that water-immiscible substances with densities less than water could be blended materials such as high-melting dense oils to form mixtures with useful densities and melting temperatures, or could be used in applications where the primary layer is less dense than the assay mixture. Many organic solvents could be used, as well as fats and waxes. Amphiphilic substances which would disperse in water on melting could be useful additives to barrier layers or primary layers (Hargreaves et al., *Biochemistry* 17:3759–3768, 1978, herein incorporated by reference)

For water-immiscible dense oils which are useful as solids in the methods of the present invention, liquification typically takes place within the range from 15° to 50° C. In some cases the temperature of liquification for meltable water-immiscible dense oils can be controlled by blending two or more substances which individually melt at higher temperatures than the mixture of the substances. It will also be apparent to those skilled in the art that liquification can be achieved in some cases by means other than melting, such as by depolymerization of a solid polymer.

Particularly preferred for centrifugal applications are primary layer materials or mixtures thereof with densities in the approximate range of 1.04 to 1.15, such as dipropyl or dibutyl phthalate, methyl cinnamate, ethyl cinnamate, butyl cinnamate, butyl citrate, diethyl fumarate, dimethyl itaconate, diethyl maleate, diethyl oxalate, diethyl succinate, and dibutyl tartrate. Where a detergent is used in the assay mixture with a liquid primary layer, the preferred primary layers include butyl phthalate, ethyl cinnamate, ethyl salicylate, silicon oil (Table 1, #38), and dimethyldiphenylpolysiloxane, because materials such as these do not form unwanted emulsions with reaction mixtures containing detergents. Where no detergent is used, the preferred primary layer materials include diethyl succinate, methyl adipate, dimethyl succinate, ethyl salicylate, dimethyl malonate, and diethyl malonate, because they readily separate into two or more clear phases when mixed with aqueous reaction mixtures that lack detergent.

Particularly preferred for embodiments in which the binding component is attached to the surface of the assay vessel are primary layers of fluorocarbon oils, because of the low viscosity and high density of these oils, which properties aid in the complete displacement of water from the binding components in such embodiments. Fluorocarbon oils are also attractive for such applications because polystyrene assay vessels can be used with such oils.

For other embodiments in which the assay vessel is desired to be clear plastic such as polystyrene, preferred primary layer materials include methyl cinnamate or methyl itaconate (stored below 36° C.), silicon oil (Table 1 #38, "high temperature" melting point bath oil, from Sigma Chemical Co., St. Louis, Mo., or from Aldrich Chemical Co., Milwaukee, Wis.), and dimethyldiphenylpolysiloxane. Preferred for embodiments in which the primary layer is desired to be in a solid form within some part of the temperature range from 15°-50° C., are primary layers containing methyl cinnamate, dimethyl itaconate, dimethyl oxalate, dimethyl succinate, dimethyl, diethyl, and dibutyl tartrate, or diphenylmethane, or mixtures of these substances. For those embodiments which utilize both centrifugal separations and solid primary layers in the range of 15°-50° C., the preferred primary layer materials are methyl cinnamate and dimethyl itaconate and mixtures of these substances.

Depending on the nature of the signal emitted or produced by the label, the washing effectiveness or supplemental reaction required, it may be desirable to include a secondary layer or layers. While a secondary layer may be formed using an appropriate water-immiscible material from Table 1, a secondary layer may also be water-soluble. To form water soluble secondary layers, or to increase the density of an assay mixture for applications such as homogeneous assays, typically a material is dissolved in water to increase its density. A representative listing of materials appropriate for this purpose is shown in Table 2. These materials are especially well suited for use as components of secondary layers of assay mixtures as described above. However, in certain instances, a material which is soluble in both water and in water-immiscible substances (e.g. formamide or dimethylsulfoxide) may be used within a primary layer. In another embodiment, formamide may be included in a DNA hybridization assay mixture and/or a primary layer for such an assay to facilitate the hybridization of polynucleotide strands.

For use with homogeneous enzyme-labeled immunoassays, an aqueous secondary layer containing enzyme substrate may have the same or similar density as the assay mixture. In such an embodiment, the primary layer will typically be a solid during incubation prior to color development. For example, if the primary layer is lens dense than both the assay mixture and the secondary layer, the primary layer will float to the top of the assay vessel upon melting. This will allow the assay mixture and the substrate-containing secondary layer to merge in the bottom of the assay vessel. In this embodiment, the primary layer material can be less dense than water if it can be solidified after dispensing onto an immiscible secondary layer or greater density. An electromagnet can be used to obtain effective mixing of the assay mixture and secondary layer after liquification of the primary layer, if several paramagnetic particles are included in the assay vessel.

Further, it may be desirable to include supplementary assay components in either primary or secondary layers which aid in signal production or detection. An example of an

TABLE 2

| CHEMICAL NAME | Representative Dense, Water-Miscible Liquids | | |
|---|---|---|---|
| | DENSITY | CONC. | COMMENTS |
| CESIUM CHLORIDE | 1.174 | 20% | |
| CESIUM SULFATE | 1.190 | 20% | |
| DIETHYLENE GLYCOL | 1.118 | 100% | |
| DIMETHYLSULFOXIDE | 1.100 | 100% | MP = 18 DEGREES |
| ETHYLENE GLYCOL | 1.114 | 100% | |
| FICOLL | 1.068 | 20% | |
| FORMAMIDE | 1.130 | 100% | MP = 2.6 DEGREES |
| GLYCEROL | 1.045 | 20% | |
| LITHIUM BROMIDE | 1.160 | 20% | SOL. IN .6 PARTS $H_2O$ |
| LITHIUM CHLORIDE | 1.113 | 20% | SOL. IN 1.3 PARTS $H_2O$ |
| LITHIUM SULFATE | NA | | SOL. IN 2.6 PARTS $H_2O$ |
| METRIZAMIDE | 1.110 | 20% | DENSITY AT 15 DEGREES |
| PERCOLL | 1.300 | 100% | SELF-FORMING GRADIENTS |
| POTASSIUM ACETATE | 1.100 | 20% | |
| POTASSIUM BROMIDE | 1.158 | 20% | |
| POTASSIUM CITRATE | 1.140 | 20% | |

TABLE 2-continued

Representative Dense, Water-Miscible Liquids

| CHEMICAL NAME | DENSITY | CONC. | COMMENTS |
| --- | --- | --- | --- |
| POTASSIUM IODIDE | NA | | |
| POTASSIUM TARTRATE | 1.139 | 20% | |
| PROPYLENE GLYCOL | 1.036 | 100% | MISC WITH $H_2O$, $CHCL_3$ |
| SODIUM BROMIDE | 1.172 | 20% | |
| SORBITOL | 1.079 | 20% | SOLUBLE TO 83% |
| SODIUM IODIDE | NA | | |
| SUCROSE | 1.079 | 20% | |

An example of an additive for a primary or secondary layer is a scintillation fluor, such as 2,5-diphenyloxazole (PPO) or 1,4-bis[5-phenyl-2-oxozolyl]benzene (POPOP), which may be included in a primary or secondary layer if the label can be detected in a scintillation counter using such fluors. Additives to a secondary layer can also include enzymes, proenzymes (zymogens), or enzyme substrate, where the label is an enzyme substrate, a zymogen activator, or an enzyme, respectively. In some embodiments (e.g. certain sandwich binding assays) where a label is added to the assay mixture after an initial incubation and separation of bound from free analyte, a secondary layer ma contain label (e.g. labelled antibody).

Secondary layers can also be formulated to contain chaotropic agents, such as salts, urea, guanidinium chloride, nonionic or ionic detergents, etc. to reduce nonspecific binding. In any case, the concentrations of these additives typically should not be sufficient to cause significant dissociation of specifically bound label from its binding component during the movement of the binding component through such layers. However, in some embodiments, dissociation of label from its binding component is desirable and can be achieved by inclusion of a suitable dissociating agent in a secondary layer. For example, sorbitol is will dissociate glycosylated hemoglobin from the boronic acid particles used in a commercial column chromatography kit from Pierce (Rockford, Illinois)

As noted above, for the purpose of the present invention, the term "cushion" is defined to include all primary or secondary layers, alone or used in combination. The volume of the cushion in different embodiments is variable and will depend on a number of factors, including the particular label employed, the detection mode, the required sensitivity of the assay, and the assay mixture volume. Both the volume and formulation or the cushion can be determined empirically. For most isotopic applications, however, a ratio of 2.5 volumes of cushion to one volume of sample will be adequate where it is required to shield radiation emanating from unbound label.

For multilayer cushion embodiments, and in cases where nonspecific binding is adequately low, the volume of the primary layer need only be enough to completely isolate the assay mixture from the secondary layer(s) under the conditions used. Where no secondary layers are used, the primary layer need only isolate binding components from the assay mixture after the separate step. A ratio of assay:cushion volumes greater the 1:1 can be used in some cases. Typically for competitive assays, approximately 3-4% nonspecific binding is acceptable, while 1-2% is very good. For sandwich assays where excess label may be used, nonspecific binding may be required to be 0.2% or below. Nonspecific binding is determined largely by the physical properties of the label and the binding components and will vary.

For example, in the use of a 96-well plate, a ratio of one volume of primary layer to one volume of sample will usually be adequate. A smaller amount of primary layer may be usable if it is in a solid form during sample loading, or if the assay mixture is immiscible with all primary and secondary layers.

The geometry and orientation of the assay vessel, the assay mixture, and the cushion will be governed by particular applications. In a typical use involving centrifugal or gravity separation, one of many types of test tubes or multiwelled plates can be used. In most uses, the sample, binding components, and secondary components are conveniently added, mixed, and incubated in contact with the predispensed primary layer. In some cases, binding components and/or secondary components can be predispensed along with the cushion in sealed assay/separation vessels. In such cases, fewer components (as few as one, the sample) need be added by the user prior to mixing and incubation.

An additional option is available with magnetic separations, wherein the cushion layer(s) can be oriented lateral to the assay mixture, or above the assay mixture if the density of assay mixture is greater than that of the layer(s).

In the case where the binding components are attached to the surface of the assay vessel, the assay mixture can be pre-equilibrated in contact with the binding components at the bottom of the assay vessel. To achieve separation of bound label from unbound label, a primary layer material can be poured or pipetted into the assay vessel to displace the less dense secondary components (including unbound label) to the top of the primary layer. In some cases, secondary layers can be added simultaneously with or subsequent to the primary layer addition.

C. Sold Phases Used In Binding Components

Binding components normally comprise two parts: a solid phase and a specific binding agent attached thereto, which confers specific binding activity. Several types of solid phases are useful in performing specific binding assays. In general they are of three types: preformed particles, the surface of a vessel, and soluble polymers which can be attached to specific binding components and which can be made insoluble during the binding assay. For each of these solid phase types, the specific binding activity may be an inherent property or it may be generated by covalent or noncovalent attachment of materials, hereinafter called "specific binding agents", which confer specific binding properties on a solid phase.

Preformed particle solid phases include stabilized microbial suspensions such as a *Staohylococcus aureus* strain which naturally produces the immunoglobulin-binding molecule, "Protein A". Alternatively, the solid phase can be non-microbial particle suspensions of minerals (hydroxyapatite, glass, or metal), beaded insoluble polymers (such as dextran [Sephadex G-10 or G-25], agarose, or polystyrene). Some of these non-microbial particles naturally exhibit useful binding activity (e.g. hydroxyapatite). However, most others must be coated with a suitable agent, using coating procedures well known is the art. These solid phases noted above can also be prepared with or may exhibit inherent magnetic or paramagnetic properties which may be exploited for separating bound from unbound label or for mixing.

Small particles confer rapid reaction kinetics on solid phase assays, but excessively small particles are not ideal for centrifugal applications. For most applications, particles should have average diameters of 0.5-3 microns and densities of 1.1 gm/mL or greater. Preferred particles have relatively uniform diameters of approximately 1 micron and densities of 1.5-3.5 gm/mL. The preferred use of micron sized microparticulate solid phases results in surprisingly fast reaction kinetics, comparable to liquid phase assays.

For gravity separation embodiments, preferred solid phase materials include very high-density particles, such as glass or plastic-coated metal beads (typically 3-6 mm diameter). Coated metal beads can easily be produced by immersing the metal beads in a solution such as polystyrene dissolved in acetone or chloroform, then draining the beads, allowing the solvent evaporate, then incubating the beads with one or more specific binding agent such as antibody, as is well known in the art.

Some particles specifically bind analyte with a non-biological mechanism. In one such embodiment, glycosylated hemoglobin binds to ion exchange particles from BioRad (Richmond, Calif.), and especially to particles with boronic acid on their surfaces such as those from Pierce Chemical Co. (Rockford, Ill.). Such particles are used for determining the percentage of this analyte in blood using column chromatography, and these or related particles are suitable for serving as binding components in the methods of the present invention.

Binding components can also be produced by precoating the assay vessel. The most stable precoated assay vessels will be produced by chemically cross-linking the molecules which contribute binding activity to each other and/or to the assay vessel surface. Such coated assay vessels (anti-IgG for mouse, rabbit, goat) are commercially available, for example, from Micromedic Systems, Inc. (Horsham, Pa.).

Alternatively, the solid phase can be produced during or subsequent to incubation of the assay mixture, by polymerization or aggregation of soluble subunits coupled to a useful binding agent. Since reactions equilibrate more rapidly when all reactants are in solution, such an approach offers shorter incubation times than traditional methods using large, preformed, insoluble binding components.

In immunoassays, binding components will typically contain specific binding agents such as antibody, antigen, protein A, avidin, or biotin, either adsorbed or chemically coupled to the solid phase. A preferred solid phase coating for immunoassays is species-specific anti-immunoglobulin (for example, goat anti-rabbit IgG). Anti-immunoglobulin coated particles can be produced using bacterial particles (Frohman et al., *J. Lab. Clin. Med.*, 93:614-621, 1979, and Bennett and O'Keefe, *J. Biol. Chem.*, 253:561-568, 1980 herein incorporated by reference). For maximum stability, such preadsorbed binding components can be chemically stabilized (e.g. with glutaraldehyde or carbodiimide) to cross-link binding agent molecules to each other and/or to the binding component particle surface. These modified "biological" solid phases have the advantage that they do not experience interference from immunoglobulin molecules such as occur at high levels in serum samples, and are commercially available (Tachiso TM, from Behring Diagnostics, La Jolla, Calif.).

Preferred particulate solid phases for centrifugal applications are those which have appropriate density and particle size to spin down rapidly through primary layer materials, preferably in standard laboratory and clinical centrifuges. These include carboxylated bromostyrene latex particles (JSR Corp, New York, N.Y.) and similar sized carboxylated magnetic copolymer particles (Seragen, Indianapolis, Ind.), and silica particles (3 micron average diameter, Baker Chemical Company). For example, these particles can be rapidly pelleted at $2000-3000 \times g$ (at $45°$ C.) using primary layers comprised of dibutyl phthalate, dimethyl cinnamate, or dimethyl itaconate. Surprisingly, the glass particles will even sediment through such primary layers without centrifugation.

Preferred also are the characteristics of low nonspecific binding of the label to be used (usually 1-2% or less) and a high, reproducibly manufacturable binding capacity (typically 10-50 microgram IgG per mL of 10% wt/v suspension). Commercial preparations of *S. aureus* (Behring Diagnostics, San Diego, Calif. and Imre Corp., Seattle, Wash.) exhibit these desirable properties. Chemically stabilized, anti-immunoglobulin coated *S. aureus* suspensions with these properties are also available from Behring Diagnostics (Tachisorb).

Other desirable solid phases for embodiments employing centrifugal separations include Sephadex G10, G15, and G25 (Pharmacia), which can be oxidized with periodate to form aldehydes suitable for chemically coupling with amino groups on proteins and other molecules. Because large molecules are excluded from the matrix of these particles, nonspecific binding of most labels is very low and can be further minimized by including in the assay solution appropriate chemical agents (such as sodium chloride $>0.1$ M).

D. Assay Methods

For simplicity, the specific binding assays of this invention will be described in terms of antigens and antibodies. However, it will be appreciated by those skilled in the art that any substantially specific binding pair can be employed in the methods of this invention, including, but not limited to, the following: the binding of complementary nucleic acid sequences; the binding of lectins with carbohydrates; the binding of hormones with receptors; the binding of vitamins with transport proteins; and the binding of immunoglobulins with nonimmunoglobulin, antibody-binding proteins.

The assays of this invention can employ any of a variety of labeling substances which are well-known in the art. Thee can include, but are not limited to, the following: radioisotopes (e.g. 32-P, 3-H, 125-I, 35-S, 14-C); enzymes (e.g. horseradish peroxidase, urease, beta galactosidase, alkaline phosphatase, glucose oxidase, enteropeptidase); fluorophores (eg. fluorescein, rhodamine, dansyl, phycobiliproteins, Nile blue, Texas red, umbelliferone); luminescers or luminescent source materials; transition metal chelates; enzyme substrates, cofactors, or inhibitors; particles (eg. magnetic, dye, high refractive index); and zymogens. These are exemplified is part by the following publications: U.S. Pat. Nos. 4,181,636; 4,401,765; 3,646,346; 4,201,763; 3,992,631; 4,160,016, U.S. patent application No. 486,016 (EP No. 0123265A1), all of which are herein incorporated by reference.

The various functional configurations in which specific binding assays can be performed are well known in the art and are described extensively in, for example, Maggio (ed.), *Enzyme Immunoassay*, CRC Press, Boca Raton, Fla., 1980, herein incorporated by reference. Several representative examples employing the methods of the present invention are described below. These methods may be used to detect the presence and/or amount of a wide variety of analytes. Representative analytes are listed in EP No. 123,265.

Briefly, in a competitive immunoassay, sample suspected of containing antigen (analyte) and a known amount of labeled antigen (tracer) compete for a limited amount of analyte-specific antibody. In heterogeneous competitive immunoassays, anti-immunoglobulin antibody or Staphylococcal protein A immobilized on a solid phase to form a binding component is added at the same time or in a subsequent step. Following incubation during which specific binding occurs, the binding component is passed through the layer(s) of the cushion, thereby separating bound label from unbound label. In homogeneous competitive enzyme-labeled assays, the assay mixture can pass through the cushion to mix with enzyme substrate color developer in a secondary layer.

The binding component (in a heterogeneous assay) or the assay mixture (in a homogeneous assay can pass through the cushion due to gravity or the assay vessel can be subjected to a centrifugal force. If the binding component is magnetizable or magnetic, the assay vessel can be subjected to a magnetic field to move the binding component through the cushion or for mixing. The presence or amount of bound label is then determined by means appropriate to the label, and is related to the presence or amount of analyte initially present in the sample, by comparison to a series of known standards. For instance, gamma counters or scintillation counters are appropriate for detecting radioisotopes, spectrophotometers are appropriate for detecting substances or solutions which absorb light, etc.

All the reagents comprising the reagent mixture (including binding components and label) can be premixed and the assay initiated by the addition of sample. In this case, the reaction typically will be allowed to substantially or completely equilibrate before the binding component or assay mixture is caused to pass through the primary layer. In such an embodiment, precise timing of the incubation period is not required. Alternatively, sample and label can be premixed and added simultaneously to the reagent mixture and incubated for a fixed interval to form a non-equilibrium assay mixture, then the binding component (for heterogeneous assays) or the entire mixture can be caused to pass through the primary layer.

A preferred alternative protocol for a competitive immunoassay is to predispense binding components comprising antibody-capture particles, as well as label, to form a reaction mixture, with analyte-specific antibody isolated in a reagent reservoir in the assay vessel. Antibody can be delivered to the assay mixture to initiate the binding reaction using, for example, low speed centrifugation. Very high precision can be expected where all reagents are factory dispensed, and where simultaneous delivery of antibody to all assay vessels in a centrifuge initiates the reaction, and where the reaction is terminated simultaneously in all assay vessels when the binding components penetrate the primary layer. When standards and controls are included in such assays, critical timing and temperature control are not necessary, a run size is limited only by the centrifuge capacity (which can exceed 200 for some microcentrifuges).

As an alternative to competitive binding assays, a heterogeneous sandwich assay can be performed. For sandwich immunoassays, analyte is incubated with two antibodies which can be present in excess, one being immobilized, or capable of being immobilized (being the binding component), and the other conjugated to a label. The antibodies can be directed against two different, non-competing determinants (epitopes) on the analyte or, if there is a multiply repeated determinant on the analyte, they can be directed to the same determinant.

Sandwich immunoassays can be carried out in simultaneous, forward, or reverse configurations (as described in U.S. Pat. No. 4,376,110, herein incorporated by reference), depending upon the order in which the analyte and the antibodies are added. Labeled antibody which is bound via analyte to the solid phase is then separated from unbound labeled antibody by passage through the cushion, as described above, and the amount of bound label determined using means appropriate to the label.

Some sandwich assays require addition of binding component, followed by separation of bound and unbound analyte, then followed by addition of label (labelled antibody). In the present invention, the addition of label to the binding component could occur in a secondary layer. This has the advantage of eliminating a manual user step in such an assay method, adding convenience and reducing the opportunity for error. Selective movement of the binding component to a specific secondary layer prior to its movement to the most distal secondary layer can be achieved using an appropriate sequence of applied forces and selection of primary and secondary layer materials to have appropriate densities. For example, low speed and high speed centrifugation could be employed to cause the binding component to pass first to an intermediate secondary layer, then to pass through more distal, denser layers. Alternatively, a water-immiscible secondary layer could be employed with a melting temperature higher than the temperature maintained during the first separation step. The temperature could be raised above the melting point of this solid secondary layer in order to complete the assay.

Sandwich assays offer the advantage that both antibodies can be present in excess, hence the sensitivity of the assay is not strictly limited by the affinity constant of the antibody(s).

In one special application of the present invention, a noncompetitive sandwich binding assay is used to detect antibody in a sample, and thus is useful in clinical serology and in screening hybridoma cultures. For example, either anti-mouse IgG or antigen can be coated on the solid phase as described above. Substantial reduction in manipulations can be achieved using the present invention compared to standard procedures used in hybridoma screening. An added advantage is that where antibody is bound to the solid phase, rapid selection of high affinity antibodies is possible by detecting binding to subnanomolar levels of labelled antigen.

E. Assay Vessels For Incubations and Separations

The vessel in which the cushion (primary and any secondary layers) is contained is referred to herein as the "assay vessel". The assay vessel may also contain one or more components of the reaction mixture. Numerous geometric configurations using different sizes and shapes of assay vessels are possible within the scope of the present invention. Referring now to FIG. 1A, in most applications the cushion, here comprising a primary layer 12, is contained within an assay vessel 10 which is closed at its distal or bottom end 13.

The assay vessel has a substantially cylindrical body 14 which defines an elongated chamber 16. The primary layer 12 extends generally transversely within the chamber to form a barrier therein, typically filling approximately $\frac{1}{8}$ to $\frac{7}{8}$, and preferably filling 15/24 to $\frac{3}{4}$ of the volume of the chamber. The optimal volume of the primary layer will be determined in part by the geometry of the assay vessel, the nature of the label, the detection method and device, if any, and the shield, if any.

Where both primary and secondary layers are utilized, typically the volume of the secondary layer will be equal to or greater than the volume of the primary layer. When more than two layers are used, the distal layer is typically the largest. It will be evident to one skilled in the art that the ratio of the volumes of primary to secondary layers used will be influenced by the nature of the particular layer materials used, and the nature of the label and binding components used. For example, where an enzyme is used as the label and an enzyme substrate is an additive to a secondary layer, the ratio of primary to secondary layers will be low (typically as low as 1:10) in order to achieve maximal sensitivity. In contrast, in the case where the label is a fluorescent material and a secondary layer is utilized to provide the optimum solvent environment for detection, the ratio can be high (typically as high as 5:1).

Suitable assay vessels include test tubes and wells, or strings of wells in a multiwell plate. It is preferred that the assay vessel be resealable at the top or proximal end 17, to protect the user and the environment from biohazards or chemical hazards in the sample or assay reagents. It is also preferred to provide the assay vessel with a penetrable septum 18. While a simple metal foil or polyethylene film is sufficient for this purpose, a seal with elastic properties such as, for example, a septum made from rubber (e.g. silicon, neoprene, or EPDM) or from a heat-meltable, moldable, rubberlike plastic (e.g. Kraton ® thermoplastic rubber from Shell Oil Co.) is preferable.

Even more preferable, for ease of manufacturing plus ease and safety in use, is a resealable septum which is penetrable by a blunt-ended instrument, such as a blunt needle or a disposable pipette tip. Particularly preferred is a resealable, elastic septum which has been molded with a thin region, or partially or completely precut with a slit, so that air can vent during the addition of liquid assay reactants. Such vessels are essentially permanently sealed at the time of manufacture, eliminate the handling of caps by the user, yet allow safe and convenient addition of assay reactants and/or sample by the user.

For radioisotopic applications, the assay vessel may be composed of polyethylene or, more preferably of polypropylene for its strength and solvent resistance.

Non-isotopic methods typically benefit from maximum clarity of the assay vessel, which can be made from glass, polystyrene, polycarbonate, nitrocellulose, and optical grade polypropylene (produced with clarifying additives from Milliken Chemicals, Spartanburg, S.C.). A surprising feature of the present invention is that test tubes composed of clear plastic such as polystyrene, which are desirable for nonisotopic assays, can be used with several of the primary layer materials even though such plastics are known to be vulnerable to damage by organic solvents and hydrocarbon oils. Adhesion of rubber and other septum materials to plastic or glass tubes can be readily accomplished. In one embodiment, a tight fitting molded cap is used with an elastic septum containing a precut slit. In another embodiment, a disk of rubber, precut with a slit, is fastened permanently to the flange at the top of a tube using methods well known in the polymer industry. For example, silicone adhesive will effectively bond silicone rubber to may kinds of tubes, including glass and some plastics. With appropriate chemical priming, polypropylene tubes can be glued to various rubbers, such as EPDM polymer blends. Cyanoacrylate adhesive will bond EPDM rubbers to polypropylene even without priming.

In one preferred embodiment especially suited for isotopic binding assays, the assay vessel is a 0.4 milliliter microcentrifuge tube (approximate dimensions 5×45 mm) composed of polypropylene, such as is commercially available from Sarstedt (Princeton, N.J.), West Coast Scientific (Emeryville, Calif.), and from numerous other manufacturers and distributors.

As shown in FIG. 1A, during use of the assay vessel, an assay mixture 24 including specific binding components 26, is placed into contact with the primary layer 12. Substantially concurrent with separation of the binding components from the unbound label in the assay mixture, the binding components will enter the primary layer and will typically continue to the distal end 13.

Figure 1B:
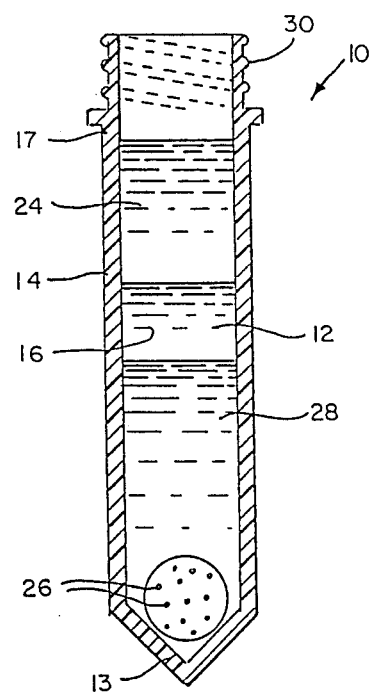
FIG. 1B is a side elevational view of an alternative assay vessel of the present invention.

Referring now to FIG. 1B, an alternative larger (2 mL) embodiment of the assay vessel 10 is shown. Other similar embodiments employ test tubes with external dimensions such as 8 by 55, 10 by 55, 10 by 75, 12 by 55, and 12 by 75 millimeters. Within this embodiment, the chamber 16 defined by the assay vessel is of a size sufficient to receive one or more preformed beads which are initially positioned on the upper surface of the primary layer 12, which is in a solid form. Specific binding agents are attached to the beads to form binding components 26. As shown in FIG. 1B, the cushion comprises a primary layer 12, and a secondary layer 28. The primary layer 12 will be the only layer to contact the assay mixture 24. Following incubation and conversion of the primary layer to a liquid form, the binding components with bound label pass through the primary layer, enter the secondary layer, and settle to the distal end 13 of the assay vessel. As an alternative to the cap 20 shown in FIG. 1A, the assay vessel may be provided with a threaded portion 30 which is mateable with a suitable cap (not shown).

In an embodiment related to that shown in FIG. 1B, employing a liquid primary layer and typically lacking secondary layers, the binding components 24 are initially positioned at the distal end of the assay vessel, and are then incubated with the other components of an assay mixture. Finally a primary layer material is poured or otherwise dispensed into the assay vessel, leaving the washed binding components and bound label at the bottom of the assay vessel, with the other components of the assay mixture (including free label) displaced to the top of the primary layer. This embodiment is also effective where the distal inner surface of the assay vessel has been coated to form the binding components.

Figure 2:
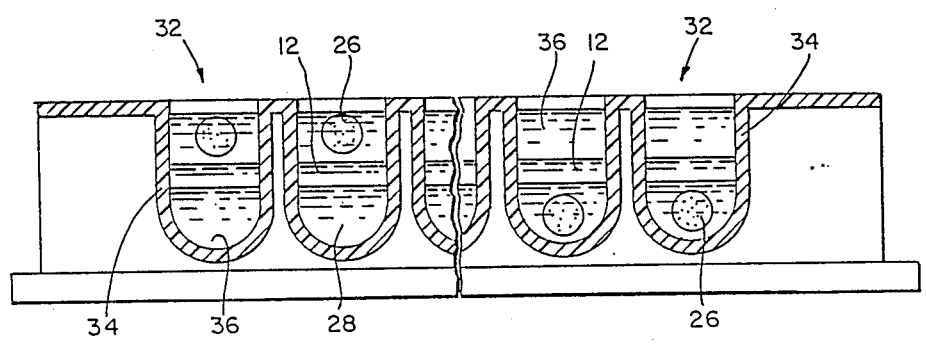
FIG. 2 is a fragmentary side elevational view of a multi-well plate assay vessel o the present invention.

Referring now to FIG. 2, another preferred embodiment is shown which is similar to that shown in FIG. 1B, with the use of a well 32 within a multiwell plate. An alternative embodiment which is preferable for some applications uses strips of 1 or 1.4 mL tubes (8 millimeter outside diameter, Skatron A.S., Lier, Norway) which fit into a standard 96 well plate array. These embodiments can be sealed with penetrable septa, are typically used with non-isotopic labels, and are appropriate for separations achieved by centrifugal, gravitational, or magnetic forces. The well 32 generally comprises a body 34 defining an open space 36. The well is of a size sufficient to receive one or more preformed beads, plus a predispensed primary layer, and some cases one or more predispensed secondary layers. In the embodiment shown in FIG. 2, the beads are initially positioned on the upper surface of the primary layer 12. The beads have specific binding agents attached thereto, thus forming binding components 26. Positioned below the primary layer is a secondary layer 28. Following incubation and conversion of the primary layer to a liquid form, the binding component(s) with bound label pass through the primary layer, enter the secondary layer, and settle to the bottom of the well. Because of the short distance from the top of the primary layer to bottom of the well, this embodiment is especially appropriate for separations employing magnetic forces.

Shielding is typically not needed in the embodiment shown in FIG. 2 because signal generation occurs only in a layer separated from the secondary components containing free label. A preferred embodiment utilizes an enzyme label, a primary layer which is in a solid form during incubation and which is converted to a liquid form prior to separation, and a secondary layer which includes an enzyme substrate which produces detectable signal in the presence of label.

In another preferred embodiment wherein the label is fluorescent and the detector "looks" up through the bottom of the well, side-excitation in the bottom region of the cushion can be used to prevent excitation of free label. Alternatively in such cases, a quenching agent (such as a resonance energy transfer receptor like rhodamine where fluorescein is the label) can be added to binding assay. The use of fluorescent quenching compounds has been described for homogeneous binding assays (Ullman and Schwarzberg, U.S. Pat. No. 3,996,345, herein incorporated by reference). Such a quencher may be useful in a heterogeneous binding assay because it will quench fluorescence of unbound label but not that of bound label, since it will be removed from the binding components by the cushion. In certain cases where the aqueous compartment of a particulate solid phase is not removed by passage through a cushion, inclusion in the assay mixture of such a quencher would be particularly useful to reduce non-specific signal.

F. Sheilds

Figure 3:
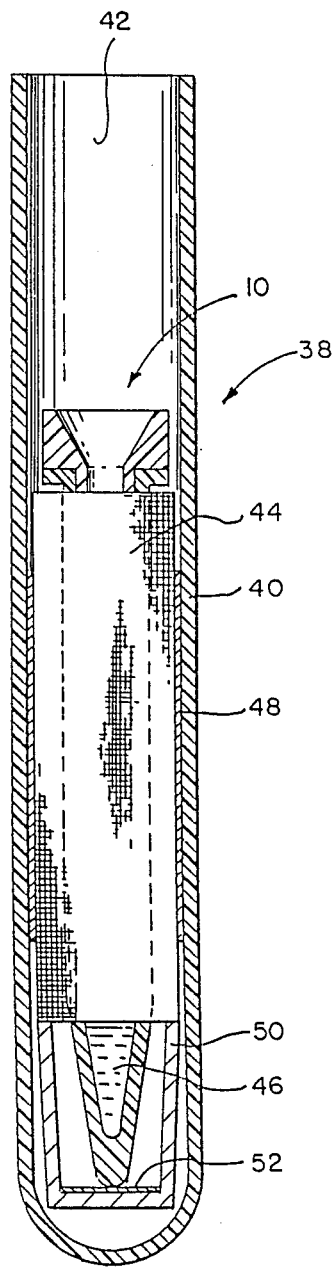
FIG. 3 is a side elevational view of a reusable detection vessel of the present invention, with an assay vessel placed therein.

Depending upon the nature of the signal emitted or produced by the label and the height of the cushion, it may or may not be desireable to physically shield the portion of the vessel containing the secondary components (with free label) in such a way that only signal emitted from the binding components is detected. Referring now to FIG. 3, a reusable detection vessel is shown with an assay vessel place therein. The detection vessel 38 generally comprises a body 40 defining an interior chamber 42. If, for example, the label is a gamma emitting isotope the upper portion (and in some cases the extreme distal end) of the detection vessel 38 could be provided with a metallic or metallized shield 44, composed preferably of lead or leaded plastic, or of copper. If the label is a fluorophore or a luminescer, the upper portion of the detection vessel could be provided with a shield composed of a light-impenetrable material. It will be apparent that in certain applications, different assay vessels and different shields will be preferable.

If shielding is desireable, the shield 44 can be either integral in the detection vessel body or it can be a separate shield, enclosed by the body of the detection vessel, into which the assay vessel 10 fits slideably. The latter configuration is generally preferred for its durability and superior geometry for shielding. For best shielding performance, the bore of the shield will typically be cylindrical and of the minimum size required for convenient insertion and removal of the assay vessel.

Referring again to FIG. 3, the assay vessel 10 fits slideably into a shield composed of a radiation-shielding material. The shield is open at both ends and has an inner diameter which is sufficiently greater than the outside diameter of the assay vessel to allow the assay vessel to slide easily into the shield. A particularly convenient configuration is one in which the assay vessel is a test tube which has a lip which engages the top of the shield and supports the tube within the shield. Microcentrifuge tubes having an approximate volume of 0.4 mL are commercially available from a number of sources and will slide easily into and out of a shield of inner diameter approximately ⅛ inch in diameter. Tubes with a similar outside diameter, but which are longer than 0.4 mL tubes, would be advantageous in certain applications.

Because in this embodiment the assay vessel is small in diameter, the shield can also be small in diameter; hence, there is comparatively little scattered radiation detected from the supernatant or the cushion. Therefore the detection of bound radioisotopic label is essentially unimpeded by the inadvertent simultaneous detection of unbound label, unlike with prior art devices and methods.

The composition of the shield will vary, depending upon the nature of the signal emitted or produced by the label, but its design and material will typically be sufficient to block detection of at least 90%, and more typically greater than 99%, and optimally greater than 99.7% of the label in the unbound fraction after separation of bound (solid) and unbound (supernatant) components of the assay mixture.

For example, if the label is a gamma-emitting isotope such as 125-Iodine, the shield might be composed of lead, leaded plastic, copper, or other suitable material. For detection instruments comprising gamma counters with annular crystals (including Micromedic Systems, Horsham, Pa., LKB Instruments, Gaithersburg, Md., and Beckman Instruments, Brea, Calif.), a sleeve of ⅛ inch thick lead (⅜ inch O.D., ¼ inch I.D.) provides an excellent combination of strength (to withstand manufacturing manipulations and centrifugation at least up to 3000×g in use) and radiation shielding. However, MacKenzie (*J. Immunological Methods*, 67:201–203, 1984, herein incorporated by reference) has calculated that a much thinner (1 mm) sheet of lead blocks 99.999964% of a dose of 125-Iodine. Thus to achieve 99.0% shielding theoretically requires a lead foil only 36 millionths of an inch thick.

High-integrity lead foils (0.006 inch and 0.012 inch thick) are commercially available. Nuclear Associates, Carle Place, N.Y.) and provide essentially complete radiation. shielding with much less weight than a ⅛ inch thick sleeve. Lead foil could be used to form a shield in applications where the ⅛ inch thick sleeve is undesirably heavy. Lead-coated or lead-containing composite plastics or fabrics, produced from molded lead or lead foil are also effective lightweight shield materials. For such foils and thin films, strength is provided by a plastic support sleeve. Other materials including non-lead metals such as brass can be used as shields for radiation including that emitted by 125-Iodine.

If the label is a beta-emitting isotope such as tritium or 32-Phosphorus, the shield might be composed of an opaque plastic. If the label is a fluorophore or a luminescer, the shield might be black plastic. However, in most applications, labels such as fluorophores and low energy beta-emitting radioisotopes will not require shields.

Where required, the shield is designed to mask approximately the upper seventy-five percent of the assay vessel and usually not more than approximately the upper ninety percent of the assay vessel. A general purpose shield will typically be as long as possible without significantly reducing the detectable label in the unshielded portion 46. For gamma counters with annular crystals and assay vessels such as shown in FIG. 1A, a ⅜ inch O.D., ⅛ inch I.D. lead sleeve approximately 1⅜ inch long is preferred. Such an assay vessel typically contains approximately 250 microliter of cushion liquid and 10 microliters or less of binding components. However, for certain detection instruments and for different cushion heights, modifications in shield length or in the volume of cushion and/or binding components will be desirable.

In cases where the detector is centered near the bottom tip of the assay tube, part or all of the assay mixture may not need to be shielded laterally because the shield below will block undesirable radiation. This form of shield is effectively a skirt, and has the added advantage that the assay mixture can be directly observed (as during reagent additions to the top of the cushion) even while shielding is in effect and the assay vessel is in its final position.

In addition to accommodating the assay vessel within itself, the shield should fit inside the body of the detection vessel, as shown in FIG. 3. The detection vessel is closed at the bottom and may or may not be sealable at the top as well. Typically, the body of the detection vessel is a test tube, the inner diameter of which is sufficiently greater than the outside diameter of the shield to allow the shield to slide tightly thereinto for purposes of semi-permanent assembly. As shown in FIG. 3, the shield may be provided with a shim 48, preferably composed of an adhesive paper label, glue, or a suitable resilient material, in order to maintain the position of the shield within the detection vessel.

Suitable for use as detection vessel bodies are test tubes of polypropylene, polyethylene, or glass, typically having approximate outer dimensions 12×75 or 12×55 mm. Such tubes are commercially available from a variety of sources and are advantageous in that they fit readily into gamma counters and/or scintillation counters. Where 0.4 mL assay vessels have tethered caps which bind on the inner walls of the detection vessel, a simple tool (e.g. Model 61-008 from the Stanley Tool Company) can be used to insert and withdraw assay vessels. Alternatively, a shorter (12×55 cm) detection vessel can be used with such assay vessels because assay vessels with tethered caps can be easily inserted and removed without a tool.

In general, plastic tubes (especially polypropylene) are preferred over glass tubes for use as detection vessel bodies because there is less risk of breakage and they can typically withstand greater centrifugal force. In general, too, it is preferred that the detection vessels be reuseable.

In a preferred embodiment for centrifugation of assay vessels directly in shields made with the ⅜ inch outside diameter lead cylinders described above, the detection vessel would contain the shield therein, supported by a cylindrical member 50. Such a cylindrical member 50 is preferably composed of plastic such as polystyrene, and may be closed at a level distal from the shield so as to support assay vessels at a constant height.

While most commercially available gamma counters exhibit good shielding using the ⅜ inch outside diameter lead cylinder described above, some with well-type crystals (especially many gamma counters having more than four crystals) require a modification in the shield design. The support cylinder closed at one end as described above can contain a shielding disk 52, made from a suitable shielding material such as lead. This disk is positioned at the bottom of the well formed by the member 50 to shield the gamma counter from unbound label radiation which is traveling generally parallel to the long axis of the assay vessel. A surprising advantage of this design is that improved shielding is obtained with all gamma counters, while causing only a slight decrease in detectability of the bound label located in the distal end of the assay vessel.

Configured in the manner described above, namely, an inner assay vessel prefilled with a cushion as described herein and slideably fitted into a shield within the body of a detection vessel, where the shield is supported by a cylindrical member, a specific binding assay can be rapidly and conveniently performed in a self-contained microtube with as little as one liquid addition (sample) step and one brief centrifugation step prior to detection of bound label. In certain instances, the centrifugation step can be eliminated. For example, one such situation is where gravity separation is employed using dense particles and a meltable primary layer. These binding assay methods can use equipment currently available in most laboratories which perform such assays. These assays can be accomplished with considerable reduction in time, skilled labor, and radioactive waste volume over specific binding assay methods as currently practiced. Comparable advantages will be experienced for both isotopic and non-isotopic applications.

G. Combined Use Of Cushions and Shields

Surprising and valuable features are inherent in the combined use of water-immiscible primary layers and radiation shields. Even the most convenient currently available isotopic assays using antibody-coated tubes or large, antibody-coated beads must be processed both before and after incubation by skilled persons or by sophisticated liquid handling equipment. Such processing includes post-incubation addition of wash solution, aspiration or decanting to remove free label, and usually a repeat of these steps. Not only are these steps inconvenient, they risk spills and contamination from both biohazards in the sample and radioactivity from the components of radioisotopic assays.

Unless carefully controlled, this washing can be disadvantageous for several reasons. First, assay precision and accuracy can suffer from dissociation of antibody-antigen complexes which occurs during the washing step, potentially reducing signal. This is especially significant with monoepitopic assays (such as with small antigens or in many assays using monoclonal antibodies), where a single attachment between antibody and antigen is formed. Furthermore, the wash liquid volume in conventional heterogeneous binding assays must be significantly larger than the volume of the assay mixture, and the larger the wash volume, the more effective the washing procedure. When this wash solution is removed, typically by decanting onto an adsorbent pad, a significant increase in radioactive waste volume is produced compared to the initial mixture volume.

A valuable and surprising feature of the present invention is that the above described wash solution can be eliminated and the reagents can be kept totally contained in the assay vessel. This feature provides improved safety compared to conventional methods because potentially hazardous materials (for example, radioactivity and/or infectious material) is totally contained for safe and convenient disposal. Subsequent to loading the assay mixture, the need for special skills or care is eliminated. Another surprising feature is that the water-immiscible layer can be small relative to the volume of the mixture, and much smaller than the typical wash volume used in traditional heterogeneous assays. As the binding components pass through the cushion, they continuously encounter fresh cushion medium and thus are effectively washed in a small volume.

The above configuration also represents a significant improvement over prior art shielding methods because the introduction of an immiscible phase between the assay mixture and the binding component dramatically increases the preciseness and completeness of separation of the bound from unbound label fractions. This immiscible phase coupled with the shielding features described above allow one to effectively perform self-contained binding assays such as radioimmunoassays. Separation of bound and unbound label in such assays is virtually instantaneous and can produce equilibrium binding assay data for applications in characterizing the tightness of interaction for binding pairs.

The geometry of the assay vessel and shield, both being elongated and relatively small in diameter, virtually eliminates the contribution of scattered radiation to the total signal measured, hence practically no mathematical correction of the data is required. Because the assay mixture and its components are immiscible in the primary layer, neither dilution nor dissociation occur during incubation of the mixture in contact with this layer, and no dissociation of binding pairs occurs as is observed in the prior art using sucrose and related materials as barriers. Thus the entire assay including mixing and incubation steps can occur in contact with the primary layer, eliminating the need to transfer the incubated mixture onto a cushion, or to controllably inject a washing solution of material such as sucrose under the incubated mixture, as in the prior art.

A further feature of the present invention is evident with the use of binding components attached to the assay vessel or to large, dense beads. A water-immiscible cushion denser than the secondary components but less dense than the large beads (if any) can be added at the end of the assay if desired, achieving separation of bound from free label without requiring the removal of unbound label and other assay mixture components from the assay vessel.

A further attribute of binding assays employing incubation of an assay mixture on a water-immiscible liquid is the dramatic reduction in the volume of the mixture. Manipulation of a visible pellet is not required and the assay mixture components can be predispensed onto the top of the primary layer. Such predispensed assay mixture component can be stored as liquids, or concentrated and/or stabilized by lyophilization, then rehydrated or diluted for use by the addition of a small (e.g. 10 microliters) sample.

Thus the assay can be miniaturized, waste dramatically reduced, and safety significantly increased, while simultaneously saving labor and reducing error-producing steps in the performance of specific binding assays.

H. Unshielded Cushion Embodiments

For unshielded applications, especially using enzyme or fluorescent labels in multiwell plates, the use of an immiscible primary layer and an aqueous secondary layer makes possible effective separation of binding components from free aqueous label (by gravity, centrifugation, or magnetic forces) over a distance too small to be effective with wholly aqueous cushions. Especially useful in such applications are primary layers which are readily solidified by cooling, or which are solid at storage and/or incubation temperatures in the range of 15°–50° C., and can be liquified (typically melted) for the separation step in this temperature range. Very dense binding component solid phase particles (e.g. glass or metal spheres) can be used which will sink through the primary layer when it is liquified by warming. It will be apparent that methods using the present invention are compatible with existing automated clinical analyzers designed for colorimetric and fluorometric clinical assays.

The following examples are offered by way of illustration, not by way of limitation.

EXAMPLES

Abbreviations used in the examples include PBS (phosphate buffered saline), BSA (bovine serum albumin), TGF-α (transforming growth factor alpha), hEGF (human epidermal growth factor), RIA (radioimmunoassay), DTT (dithiothreitol), and CPM (counts per minute).

EXAMPLE I

Miniaturized Competitive Radioimmunoassays for Transforming Growth Factor Alpha

All assays employed as assay vessels 0.4 mL microcentrifuge tubes containing 0.25–0.3 mL of cushion material Labeled peptide was produced by chloramine T iodination (specific activity ranged from 200–500 μCi/μg). Unless otherwise specified, all solid phases were prepared using *S. aureus* suspensions. Centrifugations were for 3060 seconds in a microcentrifuge at approximately 10,000×g. (A) RIA Usino Peptide fragment and Butyl Phthalate Cushion:

The synthetic peptide used for immunization of rabbits was a protein and glutaraldehyde conjugate of the c-terminus 17 amino acids of rat rTGF-α (Marquardt et al., Science 223:1079–1082, 1984). This peptide (unconjugated) was also used as a reference standard and as the label (125-iodine labeled). Antiserum or normal rabbit serum (for nonspecific binding determinations) was adsorbed onto a commercial preparation of formalin-fixed S. aureus (Imre Corp, Seattle, Wash.) to form an antibody solid phase suspension with 5% solids in PBS. Label cocktail was prepared by mixing, in 500 μL total volume, 100 μL (250,000 CPM) of labelled peptide, 100 μL of 10% (0.65 M) dithiothreitol, 30 μL of 10 mg/mL BSA, 5 μL of 10% sodium azide, 50 μL of 10×PBS, and 215 μL distilled water.

Into each assay vessel was loaded 30 μL of label cocktail, 40 μL of sample, and 30 μL of antibody suspension. After mixing the assay mixture and incubating overnight at 4° C., the assay vessels were centrifuged, then placed in radiation shields (FIG. 3) and counted in a Beckman LS-100C scintillation counter using Gammavials (Koch-Light Ltd, Suffolk, England; counting efficiency was ca. 40%).

The data obtained using synthetic peptide calibrator is shown below. Bioactive synthetic rat and human TGF-alpha gave competition curves equivalent to peptide fragment on a molar basis, with 50% competition at approximately 0.6 nM peptide.

| TGF-α RIA: PEPTIDE FRAGMENT, BUTYL PHTHALATE CUSHIONS | | |
|---|---|---|
| SAMPLE* | ANTIBODY | LABEL BOUND |
| BUFFER | ANTI-PEPTIDE FRAGMENT | 43% |
| 0.5 nM | " | 30 |
| 1.0 nM | " | 24 |
| 2.0 nM | " | 16 |
| 10 nM | " | 7 |
| BUFFER | NORMAL RABBIT SERUM | 3 |
| BUFFER | MINUS ANTIBODY SUSPENSION | 0.1 |

*final concentration in assay (B) RIA using anti-fragment antisera and bioactive synthetic peptide as tracer and reference standard, with methyl cinnamate cushions and assay reactants predispensed.

Trans-methyl cinnamate (Table 1, item 11, Aldrich Chemical Co., St. Louis, Mo.) was melted by brief heating in a microwave oven just prior to dispensing into assay vessels. The cushion solidified spontaneously at room temperature. The solid phase was prepared as in (A) above in double strength assay buffer (including 4% NP-40 nonionic detergent). This suspension was stable at 4° C. for at least one year. Label cocktail (1.5 mL) was prepared using 0.3 mL 10× assay buffer (minus nonionic detergent), 0.6 mL 10% NP-40, 0.58 mL distilled water, and 30 μL label concentrate (600,000 CPM) prepared from bioactive synthetic rat TGF-alpha (res. 1–50).

Into each assay was loaded 50 μL of reference standard sample (bioactive, synthetic rat TGF-alpha, res. 1–50), 25 μL of label cocktail, followed by 25 μL of solid phase suspension. Where indicated, all assay reactants were predispensed and equilibrated for at least 3 days at 4° C. prior to initiation of the assay by sample addition and mixing. After the indicated incubation periods, assay vessels were centrifuged and counted using radiation shields (FIG. 3, lacking disk 52) in an gamma counter (Abbott Model 200).

The temperature and mixing treatments were compared with four incubation times. One treatment consisted of incubating at 32° C., just below the melting temperature of the cushion, and mixing at 15 minute intervals. The second treatment consisted of incubating at 40°, above the melting temperature of the cushion, with mixing only at initiation of incubation (prior to warming). Both assays yielded low nonspecific binding, high specific binding, and high competition with reference standards, even after only 30 minutes of incubation. Detailed results are shown below:

| TGF-α RIA: BIOACTIVE PEPTIDES & METHYL CINNAMATE CUSHIONS | | |
|---|---|---|
| | TEMPERATURE | |
| INCUBATION TIME | 32° C. | 40° C. |
| 30 MINUTES | | |
| Nonspecific binding | 1.1% | 1.1% |
| Total bound | 24.5 | 26.5 |
| % bound with 0.3 nM sample | 21.9 | 23.8 |
| % bound with 10 nM sample | 5.6 | 6.9 |
| 60 MINUTES | | |
| Nonspecific binding | 1.1% | 1.0% |
| Total bound | 28.9 | 32.2 |
| % bound with 0.3 nM sample | 25.2 | 29.4 |
| % bound with 10 nM sample | 6.2 | 7.1 |
| 90 MINUTES | | |
| Nonspecific binding | 1.1% | 1.2% |
| Total bound | 28.7 | 34.1 |
| % bound with 0.3 nM sample | 26.2 | 32.9 |
| % bound with 10 nM sample | 6.4 | 7.6 |
| 120 MINUTES | | |
| Nonspecific binding | 1.0% | 1.1% |
| Total bound | 31.0 | 36.4 |
| % bound with 0.3 nM sample | 25.6 | 35.8 |
| % bound with 10 nM sample | 6.1 | 7.6 |

| TGF-α RIA: PREDISPENSED REACTANTS & METH. CINNAMATE CUSHIONS Incubation = 120 minutes, Temperature = 37° C., Total CPM = 7872 | | | |
|---|---|---|---|
| REACTANTS | LABEL BOUND | C.V.* | % OF MAX. BOUND |
| Buffer sample, Nonspecific binding | 1.6% (146 CPM) | 18% | N.A. |
| Buffer sample, Specific binding | 16.8 (1321 CPM) | 6% | 100% |
| 2.5 nM sample competition | 8.2 (642 CPM) | 4% | 48.6% |

*Coefficient of variation (std deviation/average), N = 6

(C) TGF-α RIA using human serum samples with anti-rabbit IgG-coated solid phase.

The assay was performed using butyl phthalate cushions as described in (A) above except that the antibody-coated solid phase was prepared either with fixed S. aureus (Pansorbin ™, Behring Diagnostics, La Jolla, Calif.) or with glutaraldehyde cross linked, anti-rabbit IgG-coated S. aureus (Tachisorb ™, Behring Diagnostics). The concentration of solids in each case was the equivalent of 12.5 μL of a 10% w/v suspension per 100 μL assay mixture volume. All tubes were prepared in duplicate and incubated for two hours at 37° C. A 50 μL sample of diluted normal human serum was added to each tube containing a predispensed cushion, followed immediately by 25 μL of labelled peptide and 25 μL of antibody solid phase suspension to initiate the reaction.

The results indicate that the even the highest concentration of human serum had no significant effect on the Tachisorb assay, while with Pansorbin even the most dilute human serum sample caused 41% nonspecific competition, presumably by displacing rabbit antibodies bound to protein A on the solid phase. With Tachisorb, non-specific binding was lower, specific binding was greater, and completion with 1.25 nM standard was greater than with Pansorbin. Detailed results are shown in Table 3 below.

TABLE 3

COMPARISON OF PANSORBIN AND TACHISORB

| ASSAY CONDITIONS | LABEL BOUND AS % OF TOTAL ADDED* | BOUND AS % OF MAXIMUM BOUND |
|---|---|---|
| Pansorbin, Normal Rabbit serum, buffer sample | 1.9 | N.A. |
| Pansorbin, Rabbit antiserum, buffer sample | 27.9 | 100 |
| Pansorbin, Rabbit antiserum, 1.25 nM Std in buffer | 16.4 | 58.9 |
| Pansorbin, Rabbit antiserum, normal human serum sample (1:10 with buffer) | 14.3 | 51.3 |
| Pansorbin, Rabbit antiserum, normal human serum sample (1:50 with buffer) | 18.1 | 64.9 |
| Pansorbin, Rabbit antiserum, normal human serum sample (1:100 with buffer) | 16.5 | 59.4 |
| Tachisorb, Normal Rabbit serum, buffer sample | 1.4 | N.A. |
| Tachisorb, Rabbit antiserum, buffer sample | 31.7 | 100 |
| Tachisorb, Rabbit antiserum, 1.25 nM STD in buffer | 18.2 | 57.4 |
| Tachisorb, Rabbit antiserum, normal human serum sample (1:10 with buffer) | 31.2 | 98.4 |
| Tachisorb, Rabbit antiserum, normal human serum sample (1:50 with buffer) | 31.6 | 99.6 |
| Tachisorb, Rabbit antiserum, normal human serum sample (1:100 with buffer) | 30.8 | 98.5 |

*Total CPM added = 8080

(D) RIA for human TGF-α using antisera recognizing the complete, bioactive synthetic hormone Synthesis of hTGF-α (1–50) peptide and immunization:

The sequence of human TGF-α as determined by DeRynck et al. (*Cell* 38:287–297, 1985) was used to synthesize the low molecular weight form of the hormone (residues 1–50) using an automated instrument (Biosearch). The resultant peptide was used to immunize rabbits repeatedly using 0.5 mg of peptide at multiple sites.

Immunoassay procedure:

The assay used reference standards and radio-iodinated tracer prepared from purified, bioactive synthetic rat TGF-alpha (Peninsula Laboratories, Belmont, Calif.). Label cocktail was prepared by mixing, in 1.5 mL total volume, 300 μL 10% buffer (0.5 M Hepes, 2 mg/mL BSA, 0.2% sodium azide), water, and 30 μL of labeled peptide (rTGF-α, 800,000 CPM). The antibody suspension was prepared essentially as described in (A) above. To each 0.4 mL tube containing 0.250.3 mL cushions of butyl phthalate was added 25 μL of label cocktail, 50 μL of sample, and 25 μL of antibody suspension. Where indicated, 10 μL of 1M DTT (freshly dissolved in 0.5 M sodium bicarbonate) was added to each assay mixture. After mixing, the tubes were incubated overnight at 4° C., then processed as described in (A) except that the detection instrument was a gamma counter (Abbott Model 200).

The assay detected rat and human synthetic TGF-α (res. 1–50) equivalently, whether or not the peptides were unfolded by reduction with DTT. Further, the assay detected authentic biological human TGF-α from cell culture media conditioned by A375 cells (Marquardt et al., *PNAS* 80:4684–4688, 1983). Detailed results are shown below:

| | PERCENTAGE OF MAXIMAL BINDING WITH COMPETITION FROM SYNTHETIC TGF-ALPHA, CORRECTED FOR NONSPECIFIC BINDING | | | | | |
|---|---|---|---|---|---|---|
| | UNREDUCED | | | REDUCED WITH DTT | | |
| CONC. IN ASSAY | RTGF, BIOACTIVE | RTGF, INACTIVE | HTGF INACTIVE | RTGF BIOACTIVE | RTGF INACTIVE | HTGF INACTIVE) |
| 0.15 nM | 83.2 | 85.2 | 82.0 | 93.8 | 92.2 | 93.2 |
| 0.32 nM | 77.3 | 76.9 | 76.9 | 87.1 | 87.7 | 89.3 |
| 0.62 nM | 68.5 | 68.9 | 70.0 | 79.9 | 82.0 | 83.2 |
| 1.25 nM | 58.5 | 58.9 | 64.4 | 74.4 | 76.0 | 78.0 |
| 2.50 nM | 54.0 | 48.2 | 54.7 | 64.9 | 70.7 | 68.6 |
| 5.00 nM | 45.7 | 40.0 | 40.6 | 47.3 | 55.9 | 59.9 |
| 1.25 nM* | | | 89.7 | | | 63.3 |

*BIOLOGICAL TGF-ALPHA, PARTIALLY PURIFIED FROM CULTURE FLUIDS (A375 CELLS)

EXAMPLE II

Enzyme-Labelled Qualitative Centrifugal Competitive Binding Assat in 0.4 ML Tubes to Detect Rabbit IGG in a Sample Using Enzyme-Labelled Rabbit Immunoglobulin and Cushions Containing Enzyme Substrate in the Bottom Layer (A) Reagents: Labelled antibody was affinity purified rabbit anti-goat immunoglobulin coupled to horseradish peroxidase (Zymed), diluted 1:3000 in phosphate buffered saline containing 1 mg/ml bovine serum albumin. The solid phase was a 10% suspension of heat-killed, formalin-fixed *S. aureus* (Imre Corp, Seattle, Wash.).

The sorbitol substrate cushion solution was prepared by dissolving 22 grams of sorbitol in 50 mLs of distilled water, then dissolving 100 mg of chromogenic substrate (OPD, from Zymed, So. San Francisco, Calif.) in one mL of water and adding 0.1 mL of the OPD stock solution and 0.1 mL of 3% hydrogen peroxide to 9.8 mLs of the sorbitol. (B) Assay: The assay vessels (0.4 mL polyethylene microcentrifuge tubes, West Coast Scientific, Emeryville, Calif.) were then loaded with 0.1 mL of the sorbitol substrate solution, then overlaid with 0.2 mL of dibutyl phthalate. Another set of assay vessels was loaded with 0.3 mL of sorbitol substrate solution.

On top of the butyl phthalate cushion was pipetted 0.05 mL of 10% pansorbin in phosphate buffered saline containing serum, then 0.05 mL of rabbit anti-goat IgG, affinity purified and labelled with horseradish peroxidase (RAG-HRP from Zymed, diluted 1:3000 in PBS containing 1 mg/mL BSA). To the other tube was added 0.005 mL dilution buffer and 0.05 mL of RAG-HRP. After two minutes, tubes were spun for one minute in a high-speed microcentrifuge (Fisher model 235B) and examined for signal development.

The control pellet was immediately "negative" (dark-brown or black) on its upper surface, while the side contacting the tube remained light amber. The pellet treated with sample was "positive" (light amber in color). No color developed in the sample layer or in the separate, clearly visible primary cushion layer, where substrate was absent. Surprisingly, only a little color developed in the lower substrate solution, but as expected the sample tube was nonetheless visibly positive (light yellow) compared to the control tube (amber). The unexpected concentration of the substrate on the surface of the solid phase itself provided a dramatic concentrating effect, amplifying the difference between positive and negative samples. While differences in the substrate solutions were apparent with careful visual examination, the pellets were easily distinguished at a glance. No further changes were seen over the next 30 minutes while the samples were kept at 25° C., but over the next 2 hours the almost black control pellet became somewhat lighter (dark brown), while the light amber sample pellet became somewhat darker (light brown or orange in color). No obvious further changes occurred, and the two pellets were easily distinguished after more than one week storage at room temperature (18°–25° C.). After extended storage, the butyl phthalate layer became amber, as if extracting the chromophore from the aqueous lower phase. The oil layer in the control tube was darker amber, distinguishable by eye from the oil layer from the sample tube.

An analogous experiment using a sorbitol substrate cushion without the intervening oil layer, and using an air space between the sample and the substrate cushion also gave visually distinguishable results. After centrifugation, no demarkation of the sample and cushion layers was visible. Washing of the solid phase was not as effective since a colored streak traced the path of the solids down the wall of the assay vessel. However, the control vessel streak, and pellet, were clearly darker amber than those in the sample vessel. With time, the entire solution (sample and cushion) became amber, though after one week the control vessel was overall still darker amber than the sample vessel.

EXAMPLE III

Miniaturized Immunoassay Using Reagents Lyophilized Onto Top Of Primary Cushion

The reactants are prepared as in example one, except that the sample is omitted and the oil is methyl cinnamate, which is a solid below 36° C. The assay vessels are frozen and subjected to lyophilization in a Speed Vac ™ (Savant) under low speed centrifugation. When the reactants are dry, tubes are stored at room temperature. When sample is added (0.05 mL), the reactants are rehydrated, and after two hours at room temperature, the tubes are warmed to 37°–40° C. and spun as in example 1 above and signal measured.

EXAMPLE IV

Detection of 32-P Labelled DNA Bound to Hydroxyapatite by Centrifugation Through a Dibytyl Phthalate Cushion Containing Scintillation Fluors (A) Reagents: $^{32}$P-labelled double-stranded DNA was divided into two aliquots. One part was boiled for ten minutes, then placed on ice. Each aliquot (20 microliters, in 10 mM Tris buffer, pH 8.2) received 100 microliters of a 10% hydroxyapatite suspension in the same buffer. Cushions were prepared in 0.4 mL microcentrifuge tubes by pipetting 0.3 mL of one of the following solutions: (1) butyl phthalate containing 40 gm/L omnifluor (New England Nuclear), (2) butyl phthalate containing 1.25 gm/L omnifluor, (3) butyl phthalate alone.

(B) Binding assay: Onto each cushion was pipetted 10 microliters of the suspension containing unheated labelled DNA and solid phase. This mixture was spun one minute in a Fisher microcentrifuge (model 235B). Tubes were counted using a Beckman LS-100C liquid scintillation counter.

| CUSHION | CPM, EACH CHANNEL | |
|---|---|---|
| | 32-P | 14-C |
| BUTYL PHTHALATE(BPH) | 85 | 67025 |
| BPH + 12.5 mg/L omnifluor | 23035 | 78835 |
| BPH + 40.0 mg/L omnifluor | 47095 | 102765 |

When counted using the 14-C channel, the 32-P was detected with or without fluor in the cushion. Counting on the 14-C channel in the presence of a ⅛ inch thick lead shield resulted in less than 10% reduction in counts, indicating that most of the DNA was bound to the solid phase under these low-salt conditions. These results indicate that, as tested here, the use of fluor-containing butyl phthalate eliminated the need for a shield, since using the 32-P channel, free label which had not entered the cushion would not be detected. These data also show that even on the 14-C channel, which gave somewhat higher signal than the 32-P channel, the inclusion of fluor in the cushion gave more than 50% greater signal compared to cushions lacking fluor. On this channel, however, a shield is required to mask the free label in the supernatant.

Even using the 32-P channel, the background signal caused by radiation from supernatant entering the cushion can be greatly reduced or eliminated by using a shield, and that the shielding is more effective than when using the 14-C channel. This is demonstrated using the heated DNA, which bound less completely to the solid phase in this series of experiments. The heated DNA was processed on butyl phthalate cushions as described above.

| CUSHION | CPM, EACH CHANNEL | |
|---|---|---|
| | 32-P | 14-C |
| BUTYL PHTHALATE(BPH) | 110, 170 | 101355, 108850 |
| BPH + shield | | 79860, 87160 |
| BPH + 40.0 mg/L omnifluor | 38255, 41305 | 132310, 141855 |
| BPH + omnifluor + shield | 25825 | 108995, 117705 |

On the 32-P channel, the lead shield with fluor-containing cushion gave almost 40% less signal the same cushion without the lead shield, indicating significant signal originating from the supernatant or upper portion of the cushion. Approximately 20% shielding of signal was obtained using the 14-C channel for the same samples.

EXAMPLE V

Use of Antibody-Coated Tubes with Displacement of Free Label by Addition of Water-Immiscible "Cushion"

Fifty microliters of either a BSA solution (1 mg/mL in PBS) or antibody against the rTGF-alpha c-terminal 17 residue fragment (prediluted 1:1000 in the same BSA solution) was added to 8×50 mm polypropylene tubes precoated with goat anti-rabbit IgG (Micromedic, Horsham, Pa.). To each of these tubes was added 50 microliters of 125-iodine labeled peptide fragment (1 nM in PBS with 0.2 mg/mL BSA). After 5 minutes at room temperature, duplicate tubes received one milliliter of either dibutyl phthalate or a fluorocarbon oil, FC40 (both from Sigma Chemical Co., St. Louis).

The dense oils displaced the aqueous assay mixtures from the bottoms of the tubes. Those with dibutyl phthalate required some agitation to dislodge droplets of aqueous assay mixtures trapped near the bottom, and a thin film of water appeared to persist between the oil and the tube inner surface. With FC40, the water floated immediately to the surface, without any apparent retention in the oil phase.

All tubes were counted immediately in a scintillation counter, using 13×50 mm plastic tubes as holders for gammavials (Koch-Light), after wrapping the supernatant and most of the oil layer in a 1.25 inch long cylinder of 0.006 inch lead foil which was supported ⅜ inch above the bottom by a plastic cylinder.

| assay mixture | primary layer material | RESULTS cpm | % bound (total) | % bound (specific) | S/N* |
|---|---|---|---|---|---|
| antibody control | butyl phthalate | 14680 3580 | 68.2 18.8 | 49.4 | 3.6 |
| antibody control | fluorocarbon oil (FC-40) | 1430 400 | 8.3 2.5 | 5.8 | 3.3 |

*S/N = signal to noise ratio

While both oils produced significant signal, they differed in performance. Butyl phthalate required some manipulation and yielded a high background, but quite high signal considering the short incubation and the relatively high antibody dilution (equilibrium binding at 1:2000 antibody dilution would be expected to yield approximately 35–40% specific binding). FC40 yielded a very low background, and a signal closer to the expected value for a 5 minute incubation. In both cases, the signal to noise ratio was similar.

EXAMPLE VI

Urine Samples from Cancer Patients Tested with TGF-Alpha (Anti-Fragment) and HEGF RIAS For the TGF assay, 2.5 mL of urine was desalted through a G15 Sephadex column (PD-10, Pharmacia) which had been equilibrated with ammonium bicarbonate buffer. The void volume fractions containing urine peptides were lyophilized and reconstituted with 120 μL of water plus 12 μL of a reducing solution containing 1 M dithiothreitol and 0.5 M sodium bicarbonate. Myeloma samples received an extra 10 μL of reducing solution and only 110 μL of water. For the hEGF assay, urine was diluted five fold with buffer.

A 0.050μ sample of each processed urine sample was mixed with 0.025 mL antibody suspension and 0.025 mL of radioiodinated tracer (full length TGF-α, residues 1–50, or hEGF, residues 1–53, 250–275 μCi/μG, approximately 10,000 cpm) in incubation/separation vessels containing 0.25 mL dibutyl phthalate. After incubating overnight at 4° C., vessels were centrifuged for 30 seconds at approximately 10,000×g and were placed into radiation shields (42 in FIG. 3) and were counted one minute in an LKB Rackgamma counter. Standards consisted full length TGF-α and hEGF in buffer containing 0.2 mg/mL bovine serum albumin and treated in the same manner as urine samples.

| SUMMARY OF TGF/EGF RESULTS USING HIGHEST NORMAL AS CUTOFF (NORMALS = 10) | | | |
|---|---|---|---|
| SAMPLE TYPE | N | POSITIVES FROM TGF | POSITIVES FROM TGF/EGF RATIO |
| BREAST | 3 | 0/3 (0%) | 1/3 (33%) |
| MYELOMA | 14 | 7/14 (50%) | 8/14 (57%) |
| PROSTATE (PROGRESSIVE) | 7 | 3/7 (43%) | 5/7 (71%) |
| PROSTATE (STABLE) | 8 | 1/8 (12%) | 1/8 (12%) |
| PROSTATE (UNRATED) | 2 | 0/2 (0%) | 0/2 (0%) |
| RECTAL | 1 | 1/1 (100%) | 1/1 (100%) |

EXAMPLE VII

Use of Multiple-Layer Cushions

Different materials of potential use as primary or secondary cushion layers were tested for their ability to maintain discrete boundaries during formation of the cushion and subsequent centrifugation, and to allow the pelleting of S. aureus particles in a brief spin. All potential cushion pellet in 0.4 mL polypropylene microcentrifuge tubes during a one minute centrifugation at full speed in a microcentrifuge (Savant, 10,000 RPM). Under these conditions, pelleting occurred equally well for sucrose solutions (10–40% w/v, d=1.0374–1.1758 at 22° C.) and the water-immiscible materials listed below: diethyl succinate, ethyl cinnamate, dibutyl phthalate, methyl adipate, and diethyl maleate.

EXAMPLE VIII

Competitive RIA for Thyroid Stimulating Hormone (TSH)

A commercial 125-iodine RIA kit for determining TSH was obtained from American Bioclinical (Portland, Oreg.) and adapted to the separation and detection methods of the present invention. All assay reactants were used according to the manufacturer's instructions except that reactant volumes were decreased four-fold, and S. aureus (25 μL of a 10% w/v suspension per test) was substituted for the "second antibody" precipitating solution. The adapted test was performed using 0.4 microcentrifuge tubes containing 0.25 mL butyl phthalate cushions.

Even though the adapted test was only incubated for two hours (37°) versus four hours (25°) for the standard test, the adapted test exhibited significantly lower nonspecific binding with equivalent total bound and greater overall sensitivity. Detailed results are given below:

unshielded counts were determined using tubes without cushions, counted without shields. Detection efficiency was determined by counting these same tubes in the two types of shields. Shielding efficiency was determined by counting tubes containing cushions with two kinds of shields (FIG. 3, with and without the disk 52).

| CPM ADDED | DETECTION OF BOUND LABEL (IN DISTAL END OF ASSAY VESSEL) | | DETECTION OF UNBOUND (IN ASSAY MIXTURE) | |
|---|---|---|---|---|
| | SHIELD | SHIELD WITH DISK | SHIELD | SHIELD WITH DISK |
| 2687 | 103% | 94% | −0.1% | 0.4% |
| 4921 | 103% | 94% | 0.2% | 0 |
| 7407 | 103% | 97% | 0.2% | 0.2% |
| 9620 | 98% | 93% | 0.1% | 0.1% |
| 12494 | 97% | 94% | 0 | 0.1% |
| 15379 | 96% | 89% | 0.1% | 0 |

(B) precision for RIA

Total bound tracer replicates were measured using

| COMPARISON OF STANDARD RIA AND ADAPTED TSH RIA | | |
|---|---|---|
| CONDITIONS | STANDARD TEST | ADAPTED TEST |
| TIME: | 4 HOURS | 2 HOURS |
| TEMPERATURE: | ROOM TEMPERATURE | 37° C. |
| ASSAY MIXTURE VOLUME: | 0.50 ML + 1 ML PRECIPITATING SOLN | .15 ML |
| USER STEPS: | 1.MIX SAMPLE+ ANTIBODY | 1.MIX SAMPLE+ ANTIBODY+TRACER |
| | 2.ADD TRACER | |
| | 3.ADD 2ND ANTIBODY | |
| | 4.SPIN 10 MINUTES | 2.SPIN 0.5 MINUTE |
| | 5.DRAIN SUPERNATANT | |
| | 6.COUNT CPM | 3.COUNT CPM |
| RESULTS | | |
| SAMPLE | STANDARD TEST % BOUND | ADAPTED TEST % BOUND |
| TOTAL CPM ADDED | N.A. | N.A. |
| NONSPECIFIC BINDING (NRS) | 3.9% | 1.7% |
| TOTAL BOUND | 37.6% | 37.2% |
| 25 μU/mL in RIA | 15.2% | N.A. |
| 33 μU/mL in RIA | 12.0% | 7.2% |
| 50 μU/mL in RIA | 7.9% | N.A. |

EXAMPLE IX

Performance pf RIA Components: Precision & Shielding Efficiency (A) Shielding effectiveness of radiation shields.

Radiation shields (42, FIG. 3) were tested for efficiency of shielding 125-iodine radiation, with and without shielding disks 52. Aliquots of 125-I containing solutions were pipetted into 0.4 mL assay vessels. Total the TGF assay (Example IA). Four groups of 15 tubes each were counted on two different gamma counters.

| MICROMEDIC FOUR-CHANNEL COUNTER (3 MINUTE COUNTS) | | | |
|---|---|---|---|
| SAMPLE SET | AVERAGE | STD DEVIATION | % CV |
| I | 2222 | 69 | 3.1 |
| II | 2121 | 85 | 4.0 |
| III | 2114 | 89 | 4.2 |
| IV | 2113 | 104 | 4.9 |
| BECKMAN ONE-CHANNEL COUNTER (ONE MINUTE COUNTS) | | | |
| SAMPLE SET | AVERAGE | STD DEVIATION | % CV |
| I | 2265 | 90 | 4.0 |
| II | 2194 | 96 | 4.0 |
| III | 2170 | 97 | 4.5 |
| IV | 2152 | 123 | 5.7 |

EXAMPLE X

Radioimmunoassay for Digoxin

A rapid assay using the present invention was compared with conventional double antibody assay methods. Commercially-available preparations of rabbit antiserum (Immunosearch, San Francisco, Calif.), and 125-Iodine labelled digoxin and digoxin standards (from Cambridge Medical Diagnostics, Cambridge, Mass.), were used. The binding component was prepared as a 10:1 blend of 10% Tachisorb TM with 10% Woods strain of *S. Aureus* (both from Behring Diagnostics, La Jolla, Calif.). The anti-digoxin antibody concentration in each assay type was adjusted to bind approximately 60% of 50,000 CPM of labelled digoxin after a fifteen minute incubation. Centrifugation was for five minutes at ca. 10,000×g in a Savant microcentrifuge with a 36-tube, fixed angle rotor. Radioactivity was determined with one minute counts. Method: To 0.4 mL polypropylene tubes containing 0.200 mL dibutyl phthalate was added 50 microliters containing labelled digoxin, 1% NGS, 5% w/v Tachisorb-R and 0.5% Sansorbin TM (Behring Diagnostics, San Diego, Calif.), and 1% NP0 (Sigma Chemicals, St. Louis, Mo.). A 50 microliter sample was added to each tube, then the assay was initiated by rapidly adding 50 microliters of antiserum diluted in 1% NGS. Tubes were capped and mixed by partially inverting several times, then incubated stationary for 15 minutes.

After centrifugation, assay tubes were transferred to radiation shields (Biotope Cat #AC-010, essentially as described in FIG. 3) and radioactivity determined in the gamma counter. Results are described below:

Results:

| PRECISION - | N = | Mean | % CV |
|---|---|---|---|
| | 18 | 1.57 ng/mL | 4.89 |
| | 18 | 0.68 ng/mL | 3.65 |
| SENSITIVITY - | .07 ng/mL (2 s.d. from "zero") | | |
| CORRELATION WITH COMMERCIAL DIGOXIN ASSAYS: | | | |
| (42 patient samples) | | | |
| versus Clinical Assays RIA | | | |
| R = 0.957748 | | | |
| slope = .953 | | | |
| intercept = 0.119 ng/mL | | | |
| versus Cambridge Medical Diagnostics RIA | | | |
| R = 0.977 | | | |
| slope = 1.014 | | | |
| intercept = −.029 ng/mL | | | |

These results are striking in that the assay of the present invention is completed in less than twenty minutes, yet correlates well with, and provides better precision than current clinical assays which take 1-2 hours to complete.

EXAMPLE XI

Enzyme Immunoassay for Digoxin

An enzyme-labelled digoxin assay using the method of the present invention is adapted from a commercial digoxin kit (Immunotech, Allston, Mass.). The only changes in reagents are the inclusion of 20% sorbitol in the color developer solution, and the substitution of 50 microliters of Tachisorb-R (Behring Diagnostics, La Jolla, Calif.) for the 500 microliters of precipitating solution (goat-anti rabbit IgG) provided with the kit.

In two mL, screw-top microcentrifuge tubes (Sarstedt, Princeton, N.J.), 1 mL of sorbitol-color developer is dispensed, then overlaid with 0.4 mL of dibutyl phthalate. A 200 microliter assay mixture is prepared by adding 100 microliters of Tachisorb-R, 25 microliters of digoxin-enzyme (alkaline phosphatase) conjugate, 25 microliters of sample (serum-based standards), and 50 microliters of antibody solution. The assay is incubated at room temperature for 15 minutes, centrifuged two minutes at 10,000×g, and further incubated one hour for color development.

Color is measured at 400 nm in a Shimadzu Model UV-160 spectrophotometer. Because of the opacity of the polypropylene tubes, results for each tube are corrected for nonspecific absorbance at 500 nm. Results are shown below:

| SAMPLE | ABSORBANCE AT 400 nm (corrected) |
|---|---|
| 0 | 180 |
| 1.0 | 150 |
| 2.0 | 100 |
| 4.0 | 80 |

In this assay, normal rabbit serum is present as a diluent for the anti-digoxin antibody, and the total IgG exceeds the capacity of the binding components added. Substantially greater signal can be obtained by optimizing the method to capture all of the analyte-specific antibody in the assay.

EXAMPLE XII

Semiqyantitative Visual Assat for Digoxin

The enzyme-labeled cushion assay adapted from the Immunotech digoxin assay was performed as described in Example XI, except that 0.4 mL assay tubes were used, with 100 microliters each of color developer and dibutyl phthalate, 25 microliters of Tachisorb-R, 25 microliters of digoxin-enzyme conjugate, 25 microliter samples, and 50 microliters of antibody solution.

After 15 minutes at room temperature, tubes were centrifuged at 10,000×g for one minute. Color initially developed in the particle pellets and gradually migrated in the liquid color developer layer. Low standards (0,1,2 ng/mL) could be distinguished visually from high standards (4,8 ng/mL) after a ten minute color development at room temperature (22 degrees C).

EXAMPLE XIII

Affinity Binding Assat for Glycosylated Hemoglobin

The principle of the test is that glycosylated hemoglobin binds to any "affinity resin", boronic acid particles (Glyco-Gel B TM) which were obtained from the Pierce Chemical Company (Rockford, Ill.). These were used as binding components in a non-immunological assay of the present invention. After centrifuging the binding components through a primary layer, bound hemoglobin was eluted with a sugar solution (15% sorbitol) contained in a secondary layer. The color in the secondary layer was measured with a spectrophotometer to provide quantified results. If the sorbitol solution was omitted, visual detection of hemoglobin bound to the solid phase was possible.

Method: Into a two mL microcentrifuge tube was pipetted 0.7 mL 15% sorbitol, then 0.3 mL primary layer material (diethylmethylmalonate), followed by 0.3 mL of a 25% (v/v) aqueous suspension of binding components. To begin the assay, 0.05 mL of hemolysed blood (1:10 dilution) was added to the particle suspension and incubated 30 minutes at room temperature or 10 minutes at 37° C. After centrifugation at 5000×g for five minutes, absorbance at 418 nm was determined using the assay vessel as a cuvette. Nonspecific absorbance at 500 nm was subtracted. Total hemoglobin or non-glycosylated hemoglobin was determined separately and the % glycosylated was calculated.

Results: Normal and elevated standards provided with a Pierce clinical diagnostics kit for glycosylated hemoglobin were consistently distinguished using both quantitative and visual detection methods. Essentially all of the bound hemoglobin is released from the particles into the sorbitol secondary layer, allowing for accurate quantitation.

I claim:

1. A method for separating bound label from unbound label within an assay mixture formed within an assay vessel, wherein said assay mixture includes one or more binding components, label bound to at least some of said binding components, and a substantially aqueous solution containing unbound label, said binding components differing in apparent density from said aqueous solution, comprising:
    contacting a primary layer with an assay mixture formed within an assay vessel, said primary layer being immiscible with both said unbound label and said binding components, and of different density than said binding components; and
    subjecting said assay mixture to conditions sufficient to cause said binding components and said unbound label to separate, based upon the comparative density of said binding components and the aqueous solution containing said unbound label.

2. The method of claim I wherein said primary layer is immiscible with water.

3. The method of claim 1 wherein said primary layer is selectively liquifiable.

4. The method of claim 1 wherein said primary layer is a mixture of two or more water-immiscible substances that are miscible with one another.

5. The method of claim 4 wherein at least one of said water-immiscible substances is selectively liquifiable.

6. The method of claim 1 wherein said primary layer is a mixture of two or more water-immiscible substances, at least one of which has a greater density than water when in liquid form.

7. The method of claim 1 wherein said assay vessel includes a barrier layer, the method including, prior to the step of contacting, contacting said barrier layer with the essay mixture and selectively allowing said assay mixture to contact said primary layer.

8. A method for separating bound label from unbound label within an assay mixture, wherein said assay mixture includes one or more binding components, non-isotopic label bound to at least some of said binding components, and a substantially aqueous solution containing unbound label, said binding components differing in apparent density from said aqueous solution, comprising:
    contacting a primary layer with an assay mixture, said primary layer being immiscible with both said bound label and said binding components, and of differing density than said binding components; and
    subjecting said assay mixture to conditions sufficient to cause said binding components and said unbound label to separate, based upon the comparative density of said binding components and the aqueous solution containing said unbound label.

9. A method for detecting the presence or amount of an analyte within a fluid sample, comprising:
    combining said fluid sample with a reaction mixture to form an assay mixture, said assay mixture formed within an assay vessel, wherein said assay mixture contains one or more binding components and label, at least some of said label and some of said analyte binding, directly or indirectly, to said binding components;
    contacting said assay mixture with a primary layer, said binding components and unbound label being immiscible with and of different density than said primary layer;
    subjecting said assay mixture to conditions sufficient to cause said binding components and said unbound label to separate, based upon the comparative density of said binding components and the assay mixture containing said unbound label; and
    detecting the label bound to said binding components and therefrom determining the presence or amount of said analyte.

10. The method of claim 9 wherein said primary layer is selectively liquifiable.

11. The method of claim 9 wherein said primary layer is a mixture of two or more water-immiscible, dense oils that are miscible with one another.

12. The method of claim 11 wherein at least one of said water-immiscible substances is selectively liquifiable.

13. The method of claim 9 wherein said primary layer is a mixture of two or more water-immiscible substances, at least one of which has a greater density than water when in liquid form.

14. The method of claim 9 wherein said binding component is a magnetic or magnetizable binding component.

15. A method for detecting the presence or amount of an analyte within a fluid sample, comprising:
    combining said fluid sample with a reaction mixture to form an assay mixture, wherein said assay mixture contains one or more binding components and non-isotopic label, at least some of said label and some of said analyte binding, directly or indirectly, to said binding components;
    contacting said assay mixture with a primary layer, said binding components and unbound label being immiscible with and of different density than said primary layer;
    subjecting said assay mixture to conditions sufficient to cause said binding components and said unbound label to separate, based upon the comparative density of said binding components and the assay mixture containing said unbound label; and
    detecting the label bound to said binding components and therefrom determining the presence or amount of said analyte.

16. The method of claim 15 wherein said binding component is a magnetic or magnetizable binding component.

* * * * *